US011266645B2

(12) United States Patent
Coffey et al.

(10) Patent No.: US 11,266,645 B2
(45) Date of Patent: Mar. 8, 2022

(54) METHODS FOR TREATING LYMPHOMA

(71) Applicant: Alexion Pharmaceuticals, Inc., Boston, MA (US)

(72) Inventors: Gregory Coffey, San Carlos, CA (US); Matthew Birrell, Lafayette, CA (US); Pamela B. Conley, Palo Alto, CA (US); John T. Curnutte, Tustin, CA (US); Anjali Pandey, Fremont, CA (US); Andrew Steele, Haslemere (GB); Glenn Michelson, Fairfax, CA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 254 days.

(21) Appl. No.: 16/403,227

(22) Filed: May 3, 2019

(65) Prior Publication Data
US 2020/0061060 A1 Feb. 27, 2020

Related U.S. Application Data

(60) Provisional application No. 62/736,047, filed on Sep. 25, 2018, provisional application No. 62/678,934, filed on May 31, 2018, provisional application No. 62/667,249, filed on May 4, 2018.

(51) Int. Cl.
*A61K 31/506* (2006.01)
*A61P 35/02* (2006.01)
*A61K 39/395* (2006.01)
*A61K 39/00* (2006.01)

(52) U.S. Cl.
CPC ........ *A61K 31/506* (2013.01); *A61K 39/3955* (2013.01); *A61P 35/02* (2018.01); *A61K 2039/505* (2013.01)

(58) Field of Classification Search
CPC .............. A61K 31/506; A61K 39/3955; A61K 2039/505; A61P 35/02

USPC ......................................................... 514/563
See application file for complete search history.

(56) References Cited

FOREIGN PATENT DOCUMENTS

WO WO-2017096303 A2 * 6/2017 ........... A61K 31/506

OTHER PUBLICATIONS

Portola Investor Room News Release, released Jun. 15, 2017 (Year: 2017).*
Furqan et al Biomarker Research, 2013, 1(5), 1-10 (Year: 2013).*
Hamlin et al., "Clinical and Correlative Results of a Phase 1 Study of Cerdulatinib (PRT062070) a Dual SYK/JAK Inhibitor in Patients with Relapsed/Refractory B Cell Malignancies", Blood, vol. 126, No. 23, Dec. 3, 2015 (Dec. 3, 2015), XP009193500, & 57th Annual Meeting of the American-Society-of- Hematology; Orlando, FL, USA; Dec. 5-8, 2015.
International Search Report and Written Opinioned dated Jul. 15, 2019 for PCT/US2019/030690, 13 pages.
Ishikawa, et al. Anti-adult T-cell leukemia/lymphoma activity of cerdulatinib, a dual SYK/JAK kinase inhibitor. Int J Oncol. Oct. 2018;53(4):1681-1690.
Ma et al., "Cerdulatinib, a novel dual SYK/JAK kinase inhibitor, has broad anti-tumor activity in both ABC and GCB types of diffuse large B cell lymphoma.", Oncotarget, vol. 6, No. 41, Nov. 5, 2015 (Nov. 5, 2015), pp. 43881-43896, XP002767267, ISSN: 1949-2553.
Steele, et al. Abstract 305: Cerdulatinib induces Bim expression and synergistic cell kill in combination with venetoclax in follicular lymphoma cell lines. Molecular and Cellular Biology/Genetics. 2018; 78(13):305.

* cited by examiner

*Primary Examiner* — Yevgeny Valenrod
(74) *Attorney, Agent, or Firm* — Sheppard Mullin Richter & Hampton LLP

(57) ABSTRACT

Compositions and methods for treating lymphoma, in particular, T-cell lymphoma and follicular lymphoma, in a human patient are provided. The methods entail administering to the patient an effective amount of cerdulatinib.

15 Claims, 15 Drawing Sheets

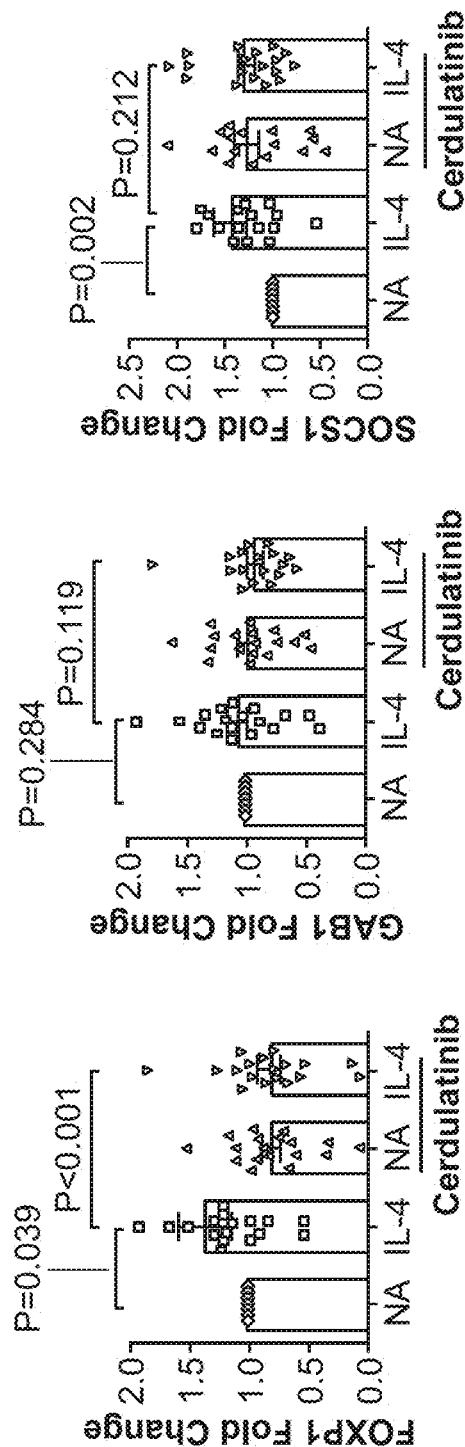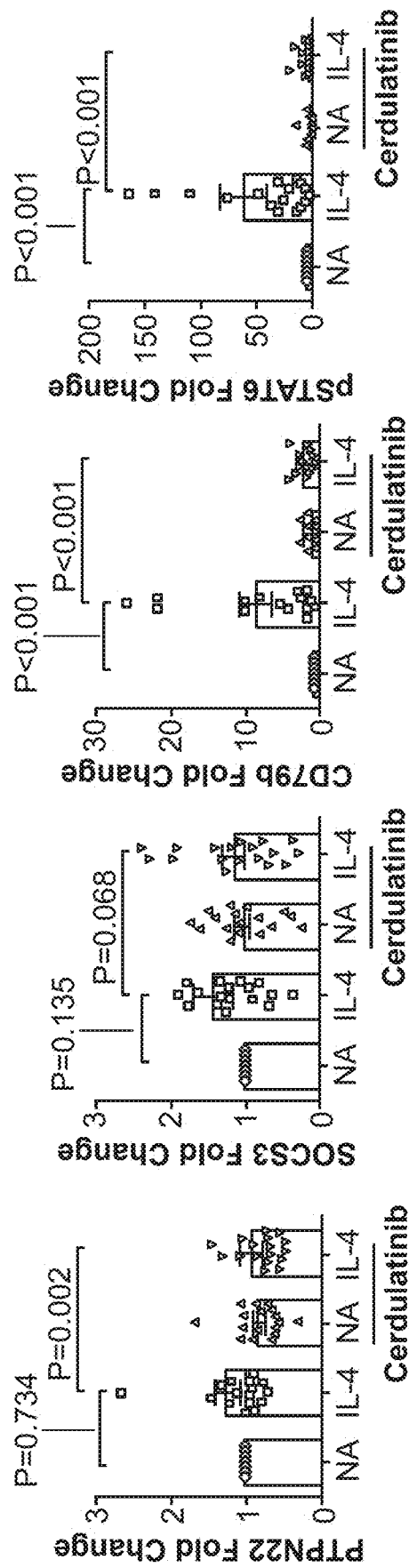

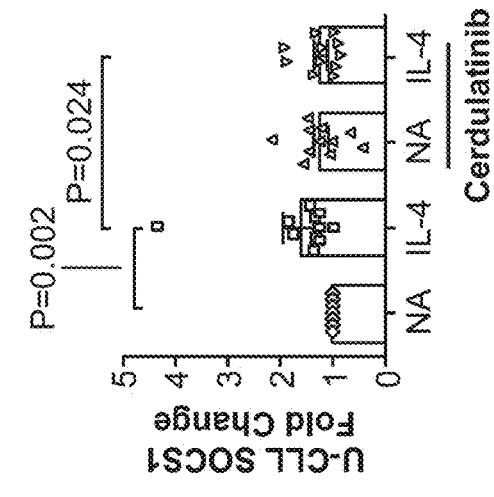
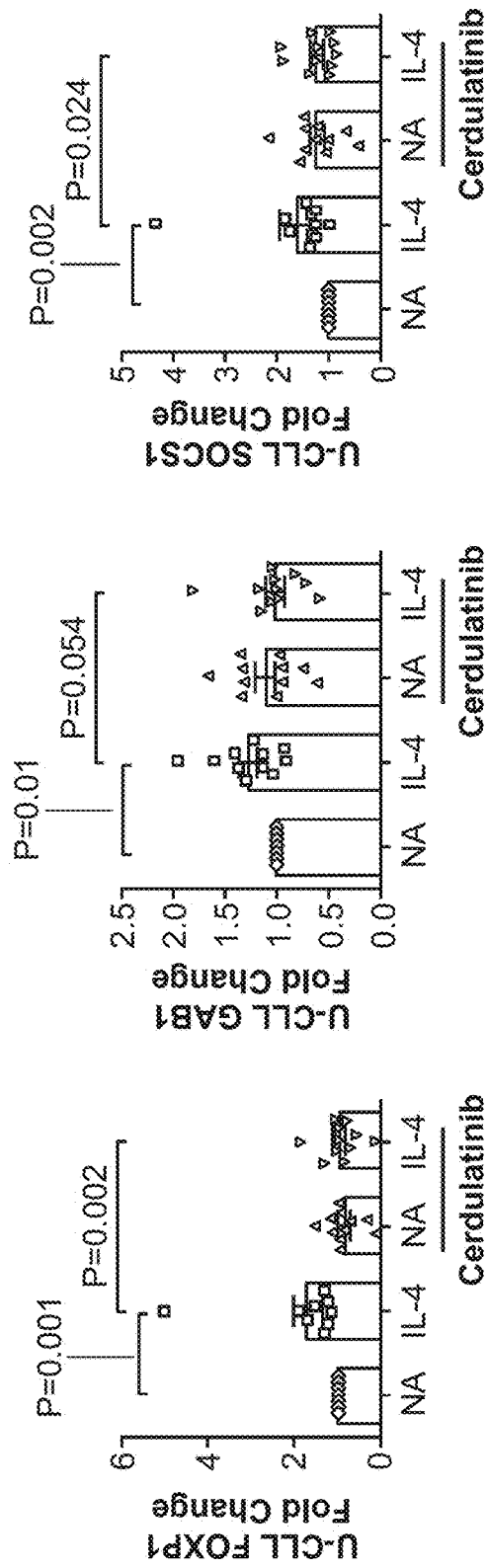
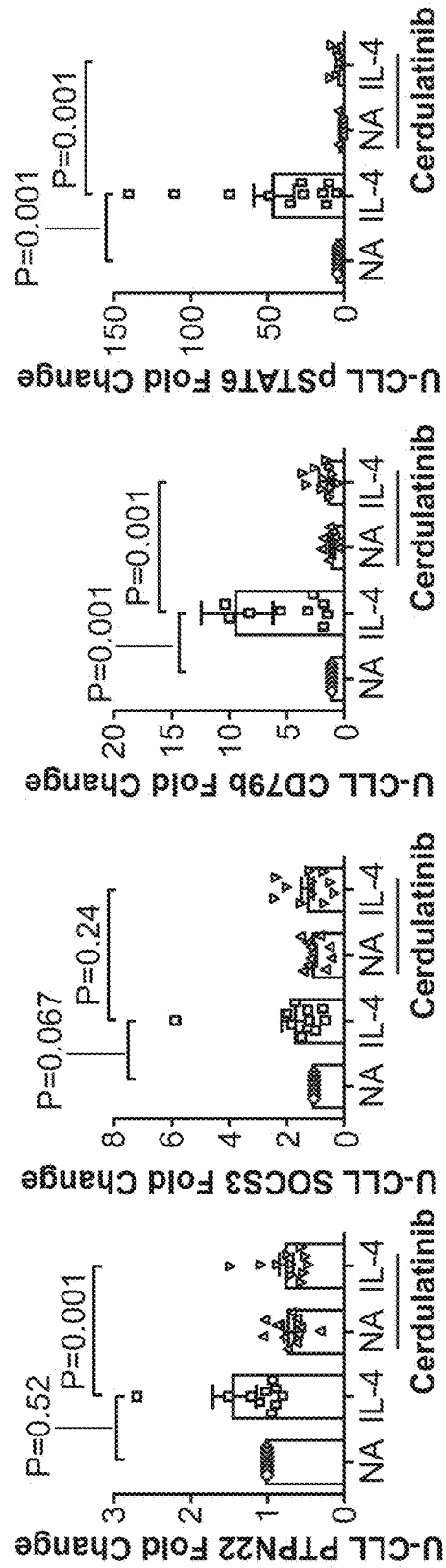
FIG. 11A
FIG. 11B
FIG. 11C
FIG. 11D
FIG. 11E
FIG. 11F
FIG. 11G

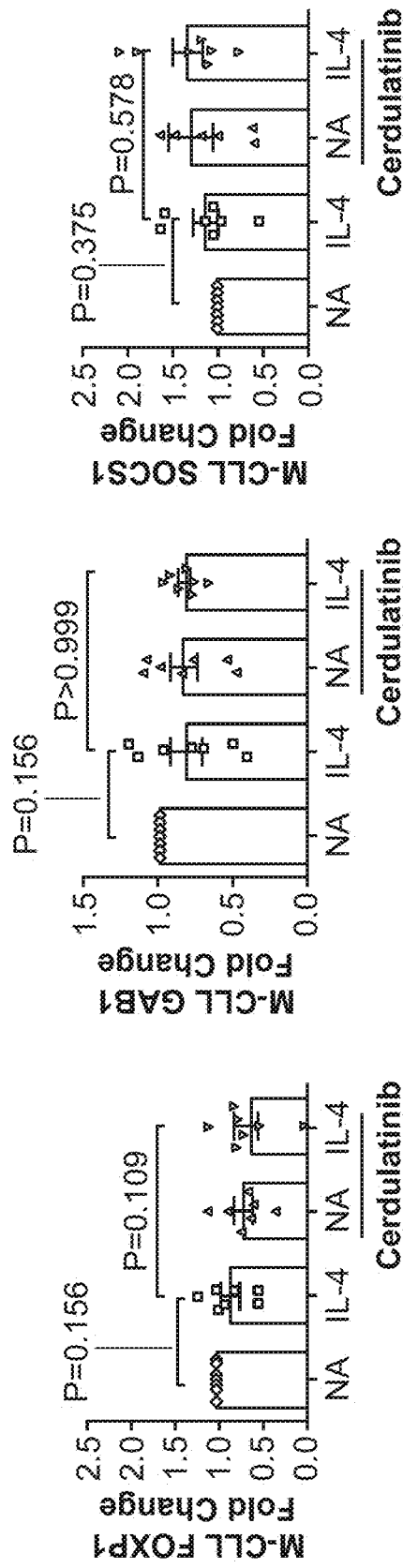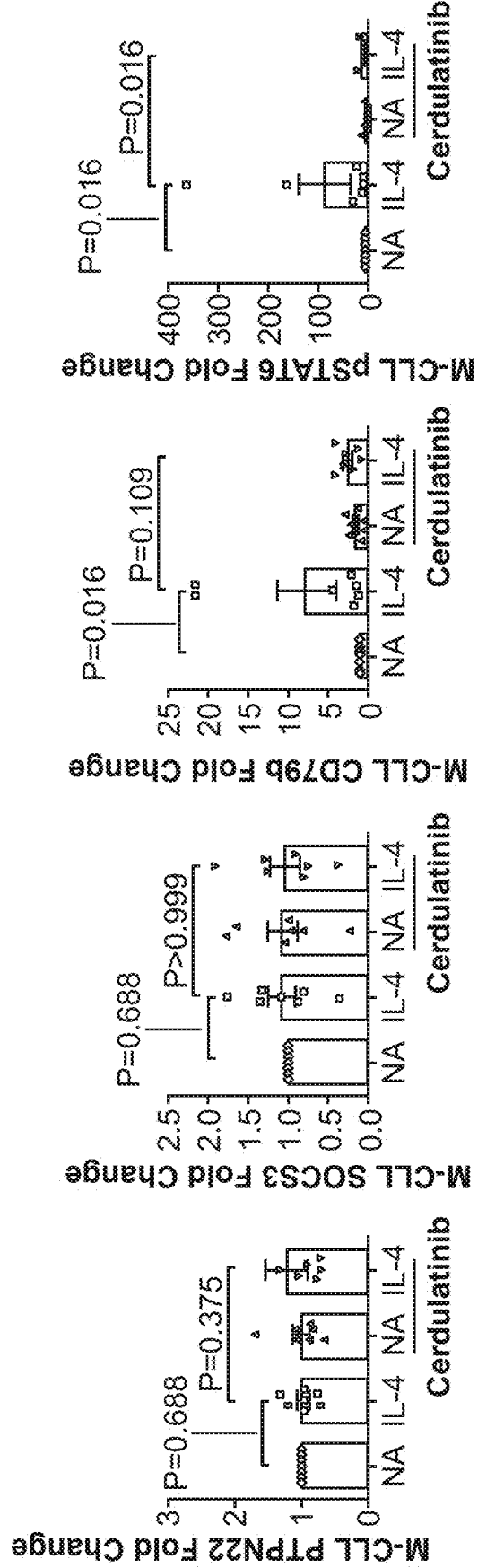
FIG. 12A  FIG. 12B  FIG. 12C  FIG. 12D  FIG. 12E  FIG. 12F  FIG. 12G

METHODS FOR TREATING LYMPHOMA

CROSS-REFERENCE TO RELATED APPLICATIONS

This application claims the benefit under 35 U.S.C. § 119(e) of U.S. Provisional Applications 62/667,249, filed on May 4, 2018, 62/678,934, filed on May 31, 2018, and 62/736,047, filed on Sep. 25, 2018, each of which is hereby incorporated by reference in its entirety.

FIELD

The present disclosure relates generally to treatment of hematological cancers, in particular lymphomas.

BACKGROUND

Lymphoma is a cancer of a part of the immune system called the lymph system. There are many types of lymphoma. One type is Hodgkin disease. The rest are called non-Hodgkin lymphomas. Non-Hodgkin lymphoma (NHL) is generally divided into two main types, based on whether its origin is B cells (B-cell lymphomas) or T cells (T-cell lymphomas).

Lymphomas as a group are the seventh-most common form of cancers, accounting for 3-4% of all cancers. Worldwide, lymphomas developed in about 566,000 people in 2012 and caused about 305,000 deaths. The five-year survival rate in the United States for all Hodgkin lymphoma subtypes is 85%, while that for non-Hodgkin lymphomas is 69%. Therefore, there remains a need for new therapies for lymphomas, especially non-Hodgkin lymphomas.

SUMMARY

The present disclosure relates to the use of cerdulatinib in the treatment of lymphomas.

Cerdulatinib is a small molecule, ATP-competitive, reversible inhibitor of both SYK and JAK family members and is described in U.S. Pat. Nos. 8,138,339 and 8,501,944. Cerdulatinib has a chemical name of 4-(cyclopropylamino)-2-((4-(4-(ethylsulfonyl)piperazin-1-yl)phenyl)amino)pyrimidine-5-carboxamide, and the structure of formula I:

I

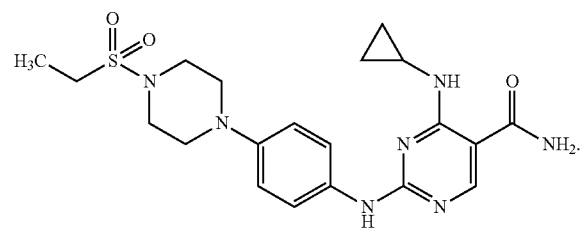

In some embodiments, provided herein is a method of treating a T-cell lymphoma in a human patient in need thereof, comprising administering to the patient an effective amount of cerdulatinib or a pharmaceutically acceptable salt, co-crystal or solvate thereof.

In some embodiments, the T-cell lymphoma is relapsed or refractory T-cell lymphoma. In some embodiments, the T-cell lymphoma has not been previously treated with an agent for treating T-cell lymphoma (i.e., treatment naive). In some embodiments, the T-cell lymphoma is T-cell non-Hodgkin lymphoma. In some embodiments, the T-cell lymphoma is relapsed or refractory T-cell non-Hodgkin lymphoma. In some embodiments, the T-cell lymphoma is peripheral T-cell lymphoma. In some embodiments, the T-cell lymphoma is relapsed or refractory peripheral T-cell lymphoma.

In some embodiments, provided herein is a method of treating a lymphoma in a human patient in need thereof and expressing one or more of Mcl-1, FoxP1, GAB1, SOCS1, or SOCS3 above a normal baseline or having (or known to have) one or more mutations in FAT4, CCND3, MYOM2, ZMYM3, NOTCH1, KMT2D, TCF3, ARID1A, AXIN1, NOTCH1, SETD2, SIGLEC10, SPEN, PCLO, TET2 (e.g., TET2$^{M66L}$), MK167, FAT3, KRAS, REL (e.g., REL$^{D354T}$), HIST1H1E (e.g., HIST1H1E$^{A47V}$), KMT2C, KMT2D, and/or SF3B1, comprising administering to the patient an effective amount of cerdulatinib or a pharmaceutically acceptable salt, co-crystal or solvate thereof.

In some embodiments, provided herein is a method of treating a lymphoma in a human patient in need thereof and having (or known to have) one or more mutations in ZMYM3, KMT2D, and FAT4, comprising administering to the patient an effective amount of cerdulatinib or a pharmaceutically acceptable salt, co-crystal or solvate thereof.

In some embodiments, the patient further has one or more mutations in BCL2, and/or BCL6.

In some embodiments, the lymphoma is follicular lymphoma (FL), transformed follicular lymphoma (tFL), diffuse large B-cell lymphoma (DLBCL), T-cell lymphoma, or mantle cell lymphoma (MCL).

In some embodiments, the lymphoma is indolent lymphoma or B cell acute lymphocytic leukemia. In some embodiments, the lymphoma is indolent lymphoma. In some embodiments, the indolent lymphoma is follicular lymphoma. In some embodiments, the indolent lymphoma is Waldenstrom's macroglobulinemia. In some embodiments, the indolent lymphoma is marginal zone lymphoma. In some embodiments, the lymphoma is B cell acute lymphocytic leukemia. In some embodiments, the lymphoma is relapsed or refractory follicular lymphoma. In some embodiments, the lymphoma is transformed follicular lymphoma. In some embodiments, the lymphoma is relapsed or refractory transformed follicular lymphoma.

In some embodiments, provided herein is a method of treating progressive chronic lymphocytic leukemia (U-CLL) or indolent chronic lymphocytic leukemia (M-CLL) in a human patient in need thereof, comprising administering to the patient an effective amount of cerdulatinib or a pharmaceutically acceptable salt, co-crystal or solvate thereof.

In some embodiments, provided herein is a method of treating chronic lymphocytic leukemia (CLL) or small lymphocytic lymphoma (SLL) in a human patient in need thereof and having (or known to have) one or more mutations in NOTCH1, SETD2, SIGLEC10, SPEN, PCLO, TET2 (e.g., TET2$^{M66L}$), MK167, FAT3, KRAS, REL (e.g., REL$^{D354T}$), HIST1H1E (e.g., HIST1H1E$^{A47V}$), KMT2C, KMT2D, and/or SF3B1, comprising administering to the patient an effective amount of cerdulatinib or a pharmaceutically acceptable salt, co-crystal or solvate thereof.

In some embodiments, provided herein is a method of treating chronic lymphocytic leukemia (CLL) or small lymphocytic lymphoma (SLL) in a human patient in need thereof and having (or known to have) one or more mutations in SETD2, SIGLEC10, SPEN, PCLO, TET2 (e.g., TET2$^{M66L}$), MK167, FAT3, KRAS, REL (e.g., REL$^{D354T}$), HIST1H1E (e.g., HIST1H1E$^{A47V}$), KMT2C, KMT2D, and/or SF3B1, comprising administering to the patient an effective amount of cerdulatinib or a pharmaceutically acceptable salt, co-crystal or solvate thereof.

In some embodiments, provided herein is a method of treating chronic lymphocytic leukemia (CLL) or small lymphocytic lymphoma (SLL) in a human patient in need thereof and having (or known to have) one or more mutations in TET2 (e.g., TET2$^{M66L}$), MK167, FAT3, KRAS, HIST1H1E (e.g., HIST1H1E$^{447V}$), KMT2C, KMT2D, and/or SF3B1, comprising administering to the patient an effective amount of cerdulatinib or a pharmaceutically acceptable salt, co-crystal or solvate thereof.

In some embodiments, the patient further has one or more mutations in SYK, JAK1, JAK2, JAK3, TYK2, TP53, STAT (e.g., STAT6$^{S864}$), A20 (e.g., A20$^{Q150R}$) and/or ATM.

In some embodiments, the patient does not have a mutation in EP300, TP53 and/or BTK. In some embodiments, the patient does not have EP300$^{S697R}$, EP300$^{C1247F}$, TP53$^{N285K}$, TP53$^{R273C}$ and/or BTK$^{C481S}$.

In some embodiments, provided herein is a method of treating a follicular lymphoma or indolent non-Hodgkin's Lymphoma (iNHL) in a human patient in need thereof, comprising administering to the patient an effective amount of cerdulatinib or a pharmaceutically acceptable salt, co-crystal or solvate thereof to achieve and maintain a steady state minimum plasma cerdulatinib concentration of between about 0.05 µM to about 3 µM in the patient.

In some embodiments, provided herein is a method of treating a chronic lymphocytic leukemia or small lymphocytic lymphoma in a human patient in need thereof, comprising administering to the patient an effective amount of cerdulatinib or a pharmaceutically acceptable salt, co-crystal or solvate thereof to achieve and maintain a steady state minimum plasma cerdulatinib concentration of between about 0.05 µM to about 3 µM in the patient.

In some embodiments, provided herein is a method of treating a marginal zone lymphoma, Waldenstrom's macroglobulinemia, chronic lymphocytic leukemia or small lymphocytic lymphoma in a human patient in need thereof, comprising administering to the patient an effective amount of cerdulatinib or a pharmaceutically acceptable salt, co-crystal or solvate thereof to achieve and maintain a steady state minimum plasma cerdulatinib concentration of between about 0.05 µM to about 3 µM in the patient.

In some embodiments, provided herein is a method of treating a lymphoma in a human patient in need thereof comprising administering to the patient an effective amount of cerdulatinib or a pharmaceutically acceptable salt, co-crystal or solvate thereof and an effective amount of a Mcl-1 inhibitor or a pharmaceutically acceptable salt, co-crystal or solvate thereof.

In some embodiments, provided herein is a use of cerdulatinib or a pharmaceutically acceptable salt, co-crystal or solvate thereof in a treatment method described herein.

In some embodiments, provided herein is a use of cerdulatinib or a pharmaceutically acceptable salt, co-crystal or solvate thereof in the manufacture of a medicament for use in a treatment method described herein.

In some embodiments, provided herein is a method of treating a lymphoma in a human patient in need thereof, comprising administering to the patient an effective amount of cerdulatinib or a pharmaceutically acceptable salt, co-crystal or solvate thereof and an effective amount of rituximab.

In some embodiments, provided herein is a use of cerdulatinib or a pharmaceutically acceptable salt, co-crystal or solvate thereof and rituximab in a treatment method described herein.

In some embodiments, provided herein is a composition comprising an effective amount of cerdulatinib or a pharmaceutically acceptable salt, co-crystal or solvate thereof and an effective amount of rituximab.

In some embodiments, provided herein is a use of cerdulatinib or a pharmaceutically acceptable salt, co-crystal or solvate thereof and rituximab in the manufacture of a medicament for use in a treatment method described herein.

BRIEF DESCRIPTION OF THE DRAWINGS

FIG. 9A and FIG. 9B show immunoblots demonstrating protein expression among progressive (U-CLL) (FIG. 9A) and indolent CLL (M-CLL) (FIG. 9B) cell lines, respectively, following treatment with and without IL-4 in the presence or absence of cerdulatinib.

FIG. 10A, FIG. 10B, FIG. 10C, FIG. 10D, FIG. 10E, FIG. 10F, and FIG. 10G are summary of the immunoblot densitometry indicating changes in expression of FOXP1 (FIG. 10A), GAB1 (FIG. 10B), SOCS1 (FIG. 10C), PTPN22 (FIG. 10D), SOCS3 (FIG. 10E), CD79b (FIG. 10F), and pSTAT6 (FIG. 10G), respectively, in CLL cells following treatment with and without IL-4 in the presence or absence of 1 µM cerdulatinib as compared with control. In each of FIG. 10A, FIG. 10B, FIG. 10C, FIG. 10D, FIG. 10E, FIG. 10F, and FIG. 10G, the bars from left to right represent control, IL-4 treatment alone, cerdulatinib treatment alone and IL-4+cerdulatinib, respectively.

FIG. 11A, FIG. 11B, FIG. 11C, FIG. 11D, FIG. 11E, FIG. 11F, and FIG. 11G are summary of the immunoblot densitometry indicating changes in expression of FOXP1 (FIG. 11A), GAB1 (FIG. 11B), SOCS1 (FIG. 11C), PTPN22 (FIG. 11D), SOCS3 (FIG. 11E), CD79b (FIG. 11F), and pSTAT6 (FIG. 11G), respectively, in progressive CLL cells following treatment with and without IL-4 in the presence or absence of 1 µM cerdulatinib as compared with control. In each of FIG. 11A, FIG. 11B, FIG. 11C, FIG. 11D, FIG. 11E, FIG. 11F, and FIG. 11G, the bars from left to right represent control, IL-4 treatment alone, cerdulatinib treatment alone and IL-4+cerdulatinib, respectively.

FIG. 12A, FIG. 12B, FIG. 12C, FIG. 12D, FIG. 12E, FIG. 12F, and FIG. 12G are summary of the immunoblot densitometry indicating changes in expression of FOXP1 (FIG. 12A), GAB1 (FIG. 12B), SOCS1 (FIG. 12C), PTPN22 (FIG. 12D), SOCS3 (FIG. 12E), CD79b (FIG. 12F), and pSTAT6 (FIG. 12G), respectively, in indolent CLL cells following treatment with and without IL-4 in the presence or absence of 1 µM cerdulatinib as compared with control. In each of FIG. 12A, FIG. 12B, FIG. 12C, FIG. 12D, FIG. 12E, FIG. 12F, and FIG. 12G, the bars from left to right represent control, IL-4 treatment alone, cerdulatinib treatment alone and IL-4+cerdulatinib, respectively.

DETAILED DESCRIPTION

Figure 1:
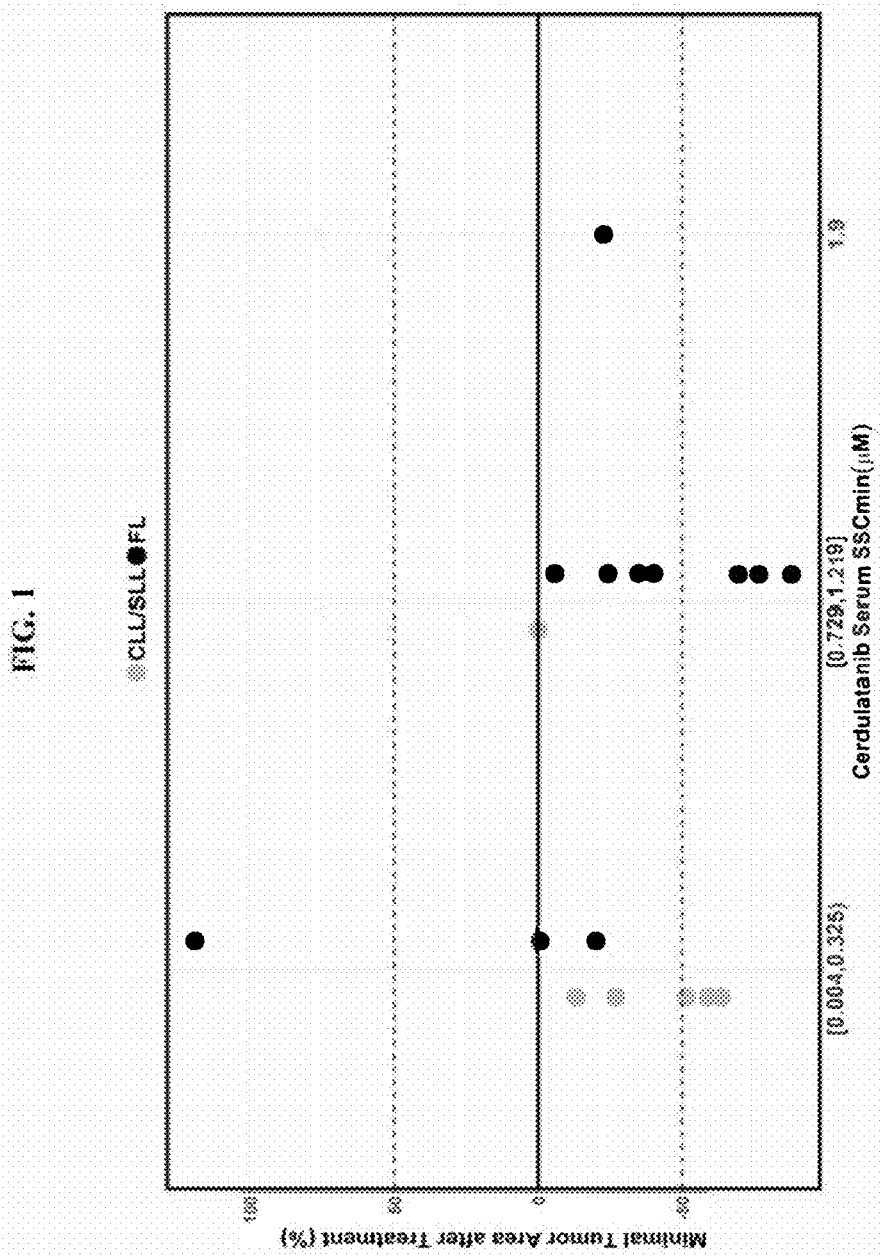
FIG. 1 shows tumor response to cerdulatinib and association with exposure in CLL/SLL and FL patients.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

1. Definitions

Unless defined otherwise, all technical and scientific terms used herein have the same meaning as commonly understood by one of ordinary skill in the art to which this disclosure belongs. As used herein the following terms have the following meanings.

It must be noted that as used herein and in the appended claims, the singular forms "a", "an", and "the" include plural referents unless the context clearly dictates otherwise. Thus, for example, reference to "an agent" includes a plurality of agents.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., amount, and concentration, including range, indicates approximations which may vary by (+) or (−) 10%, 5% or 1%.

As used herein, the term "treating" refers to preventing, curing, reversing, attenuating, alleviating, minimizing, suppressing or halting tumor growth, spreading, metastasis, or development.

As used herein, the term "patient" refers to a subject having a cancer or tumor, which can be benign or malignant. In certain embodiments, the patent is a human or an animal.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier" refers to pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to the cancerous tissue or a tissue adjacent to the cancerous tissue.

As used herein, the term "pharmaceutically acceptable salt" refers to any acid or base addition salt whose counterions are non-toxic to the patient in pharmaceutical doses of the salts. A host of pharmaceutically acceptable salts are well known in the pharmaceutical field. If pharmaceutically acceptable salts of the compounds of this disclosure are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulphates, phosphates, nitrates, sulphamates, malonates, salicylates, methylene-bis-b-hydroxynaphthoates, gentisates, isethionates, di-p-toluoyltartrates, ethanesulphonates, cyclohexylsulphamates, quinates, and the like. Pharmaceutically acceptable base addition salts include, without limitation, those derived from alkali or alkaline earth metal bases or conventional organic bases, such as triethylamine, pyridine, piperidine, morpholine, N-methylmorpholine, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

As used herein, the term "formulated" or "formulation" refers to the process in which different chemical substances, including one or more pharmaceutically active ingredients, are combined to produce a dosage form. In certain embodiments, two or more pharmaceutically active ingredients can be co-formulated into a single dosage form or combined dosage unit, or formulated separately and subsequently combined into a combined dosage unit. A sustained release formulation is a formulation which is designed to slowly release a therapeutic agent in the body over an extended period of time, whereas an immediate release formulation is a formulation which is designed to quickly release a therapeutic agent in the body over a shortened period of time.

As used herein, the term "delivery" refers to approaches, formulations, technologies, and systems for transporting a pharmaceutical composition in the body as needed to safely achieve its desired therapeutic effect. In some embodiments, an effective amount of the composition is formulated for delivery into the blood stream of a patient.

Abbreviations:
ABVD doxorubicin, bleomycin, vinblastine, and dacarbazine
AUC area under curve
BEAM carmustine, etopside, cytarabine, and melphalan
BID: once daily CHOP cyclophosphamide, doxorubicin, vincristine, and prednisone
$C_{max}$ maximum (or peak) concentration
$C_{min}$ minimum (or trough) concentration
CR: complete response
EPOCH etoposide, prednisone, vincristine, cyclophosphamide and doxorubicin
$IC_{50}$ half maximal inhibitory concentration
mg milligram
mL milliliter
ORR: overall response rate
PD progressive disease
pg picogram
PR: partial response
QD: twice daily
SD stable disease
$SSC_{min}$ steady state $C_{min}$
μL microliter
μM micromolar 2. Methods of Treatment Provided herein are methods of treating lymphomas with cerdulatinib.

Cerdulatinib is a small molecule, ATP-competitive, reversible inhibitor of both SYK and JAK family members. Cerdulatinib has a chemical name of 4-(cyclopropylamino)-2-((4-(4-(ethylsulfonyl)piperazin-1-yl)phenyl)amino)pyrimidine-5-carboxamide or 4-(cyclopropylamino)-2-({4-[4-(ethanesulfonyl)piperazin-1-yl]phenyl}amino)pyrimidine-5-carboxamide, and the chemical structure of formula I:

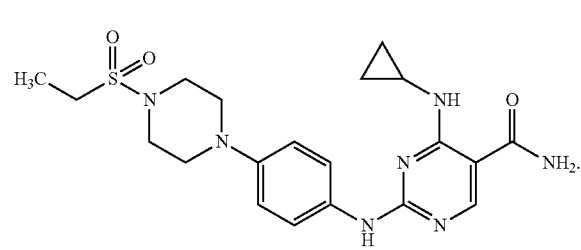

I

Treatment of T-Cell Lymphoma

In some embodiments, provided herein is a method of treating a T-cell lymphoma (TCL) in a human patient in need thereof, comprising administering to the patient an effective amount of cerdulatinib or a pharmaceutically acceptable salt, co-crystal or solvate thereof.

There are many different forms of T-cell lymphomas, some of which are aggressive (fast-growing) and some of which are indolent (slow-growing). T-cell lymphomas include immature T-cell lymphoma, such as T-cell lymphoblastic lymphoma (T-LBL), and mature T-cell lymphomas, such as peripheral T-cell lymphoma (PTCL).

Peripheral T-cell lymphomas (PTCLs), developed in mature white blood cells called T-cells, are aggressive types of non-Hodgkin lymphoma (NHL) with a median survival of less than 5 years, and typically have a poorer prognosis compared to their B cell counterparts. O'Connor, O. A., et al., *Changing the Paradigms of Treatment in Peripheral T-cell Lymphoma: From Biology to Clinical Practice*. Clin Cancer Res, 2014. 20(20):5240-5254; Swerdlow, S. H., et al., *The 2016 revision of the World Health Organization classification of lymphoid neoplasms*. Blood, 2016. 127(20): 2375-2390; Gaulard, P., and de Leval, L., *Pathology of Peripheral T-Cell Lymphomas: Where Do We Stand? Seminars in Hematology*, 2014. 51(1):5-16. In general, patients with PTCL have an inferior survival when compared to patients with B-cell NHL. Swerdlow, S. H., et al., *The 2016 revision of the World Health Organization classification of lymphoid neoplasms*. Blood, 2016. 127(20):2375-2390; Vose, J. M., et. al, *International Peripheral T-Cell and Natural Killer/T-Cell Lymphoma Study: Pathology Findings and Clinical Outcomes*. Journal of Clinical Oncology, 2008. 26(25):4124-4130; Gisselbrecht, C., et. al, *Prognostic Significance of T-Cell Phenotype in Aggressive Non-Hodgkin's Lymphomas. Blood*, 1998. 92(1):76-82.

Front-line therapy for PTCL is typically CHOP (cyclophosphamide, doxorubicin, vincristine, prednisone) or CHO(E)P in which etoposide is included, or other intense chemotherapy, albeit with outcomes inferior to those described in B-cell malignancies. The majority of patients relapse following standard therapy, and overall survival (OS) remains low. For PTCL patients (other than ALCL) who relapse after, or are refractory to, frontline therapies, median OS is 6 months. Mak, V., et. al., *Survival of patients with peripheral T-cell lymphoma after first relapse or progression: spectrum of disease and rare long-term survivors*. J Clin Oncol, 2013. 31(16):1970-1976.

A limited number of options exist for patients who fail frontline chemotherapy. In the United States, belinostat (HDAC inhibitor), pralatrexate (anti-folate), and romidepsin are approved for patients with relapsed or refractory PTCL, which have poor overall response rates (ORRs) of approximately 25%, with a complete response (CR) rate of 8 to 15% and a median duration of response (DOR) up to 12 months, see Table 1.

TABLE 1

| Clinical Data for the Agents Approved for Relapsed/Refractory PTCL | | | | |
|---|---|---|---|---|
| | Pralatrexate [a] | Romidepsin [b] | Belinostat | Brentuximab [c] |
| Mechanism of Action | Anti-folate | HD AC inhibitor | HDAC inhibitor | CD30-directed antibody-drug conjugate |
| Approval Year | 2009 | 2011 | 2014 | 2011 |
| Dosing and Administration | 30 mg/m² IV infusion over 3 to 5 minutes once weekly for 6 weeks in 7-wk cycles. | 14 mg/m² IV infusion over a 4-hour period on Days 1, 8, and 15 of a 28-day cycle. | 1,000 mg/m², 30 minute IV infusion on Days 1-5, q3w (21-day cycles). | IV infusion over 30 minutes every 3 weeks. 1.8 mg/kg up to a maximum of 180 mg. |

TABLE 1-continued

Clinical Data for the Agents Approved for Relapsed/Refractory PTCL

|  | Pralatrexate [a] | Romidepsin [b] | Belinostat | Brentuximab [c] |
|---|---|---|---|---|
| Clinical Trial Patient Number | 115 | 131 | 129 | 58 |
| Efficacy Results | ORR: 27% (6% CR) DOR: 9.4 months | ORR: 26% (13% CR) DOR: 11-15 months | ORR: 26% (11% CR) DOR: 8.4 months | ORR: 86% (57% CR) DOR: 12.6 months |
| Safety (Grade 3/4 AEs) | Thrombocytopenia: 33% Mucositis: 21% Neutropenia: 20% Anemia: 17% Fatigue: 7% | Thrombocytopenia: 21% Fatigue: 13% Nausea: 4% | Anemia: 11% Thrombocytopenia: 7% Fatigue: 5% | Neutropenia: 21% Peripheral sensory neuropathy: 10% Thrombocytopenia: 10% |

[a] FOLOTYN ® (pralatrexate injection) package insert; Westminster, CO; Alios Therapeutics. Inc. 2016;
[b] ISTODAX ® and (romidepsin) package insert; Summit, NJ; Celegene Corporation, 2016;
[c] approved only for anaplastic large cell lymphoma.

In comparison, cerdulatinib treatment (e.g., 30 mg BID) in a clinical trial achieved a 47% ORR and CR were observed in 5/15 evaluable patients (33%), representing diverse subtypes of PTCL. Importantly, partial response (PR) and CR occurred in patients refractory to multiple lines of therapy, including pralatrexate, romidepsin, belinostat, and an investigational PI3K inhibitor.

The safety profile of cerdulatinib is both predictable and manageable. The safety data for PTCL (n=16) includes 4 study drug-related Serious Adverse Events (SAEs) which were Grade 3 to 4 in 8 patients with no deaths or discontinuations in the PTCL patients due to Treatment Emergent Adverse Events (TEAEs). Table 2 shows a comparison the safety data of cerdulatinib and FDA approved drugs in PTCL patents.

TABLE 2

Toxicities ≥ Grade 3 in Approved Agents for r/r PTCL vs. Cerdulatinib

|  | Romidepsin N = 121 | Belinostat N = 139 | Pralatrexate N = 115 | Brentuximab N = 58 | Cerdulatinib N = 16 |
|---|---|---|---|---|---|
| Mucositis | — | — | 23% | — | — |
| Infection | 19% | 8.5% | — | — | 18.8% |
| Sepsis | 5% | — | 5% | — | — |
| Asthenia/Fatigue | 8-19% | 5% | 8% | 4% | 6.3% |
| Pyrexia | 6-17% | 2% | 2% | 2% | — |
| Thrombocytopenia | 24-36% | 7% | 33% | 10% | — |
| Neutropenia | 20-47% | — | 20% | 21% | 6.3% |
| Anemia | 11-28% | 11% | 17% | 2% | — |
| Leukopenia | 6-45% | — | 7% | — | — |
| Diarrhea/Colitis | — | — | — | 3% | 6.3% |

Peripheral T-cell lymphomas include various subtypes, such as peripheral T-cell lymphoma not otherwise specified (PTCL-NOS), angioimmunoblastic T-cell lymphoma (AITL), follicular T-cell lymphoma (FTCL), anaplastic large cell lymphoma (ALCL), enteropathy-associated T-cell lymphoma (EATL), adult T-cell leukemia/lymphoma (ATLL), nasal NK/T-cell lymphoma, hepatosplenic T-cell lymphoma, cutaneous (skin) T-cell lymphoma (CTCL), and are grouped into three categories: nodal, extranodal and leukemic.

Peripheral T-cell lymphoma not otherwise specified (PTCL-NOS) refers to a group of aggressive diseases that do not fit into any of the other subtypes of PTCL. PTCL-NOS is the most common PTCL subtype, making up about one-quarter of all PTCLs. Most patients with PTCL-NOS are diagnosed with their disease confined to the lymph nodes. Sites outside the lymph nodes, such as the liver, bone marrow, gastrointestinal tract, and skin, may also be involved.

Anaplastic large cell lymphoma (ALCL) is an aggressive T-cell lymphoma that accounts for approximately 12% to 15% of all T-cell lymphomas in adults and between 10% and 30% of all lymphomas in children. It can be divided into three types: two systemic (presents in lymph nodes or organs) subtypes and one non-systemic type. The systemic subtypes are anaplastic lymphoma kinase (ALK) positive anaplastic large cell lymphoma (an abnormal form of the ALK protein is present on the surface of the lymphoma cells) or ALK negative anaplastic large cell lymphoma (an abnormal form of the ALK protein is absent on the surface of the lymphoma cells). The non-systemic type appears only on the skin and is called primary cutaneous anaplastic large cell lymphoma. The systemic types are usually fast-growing, while the non-systemic type is usually more slow-growing.

Angioimmunoblastic lymphoma (AITL) is an aggressive T-cell lymphoma accounting for 15% to 18% of all T-cell lymphomas in the United States. Symptoms of AITL include high fever, skin rash, night sweats, and autoimmune disorders such as autoimmune hemolytic anemia (AIHA) and immune thrombocytopenia (ITP). As a result of these autoimmune disorders, the body's immune system does not recognize, and consequently destroys, its own cells and tissues, such as red blood cells (in the case of AIHA) or platelets (in the case of ITP). Stage I AITL is localized and has not spread beyond the tumor. Stage II affects only a nearby lymph node. In stage III, affected lymph nodes are found both above and below the diaphragm. In stage IV, one or more organs beyond the lymph nodes are affected, such as the bone, bone marrow, skin, or liver.

Cutaneous T-cell lymphoma (CTCL) is a group of typically slow-growing cancers that appear on, and are most often confined to, the skin. The most common type of cutaneous T-cell lymphoma is mycosis fungoides, which appears as skin patches or plaques. Other types include Sézary syndrome, primary cutaneous anaplastic large cell lymphoma and lymphomatoid papulosis.

Adult T-cell leukemia/lymphoma (ATLL) is a rare form of T-cell lymphoma linked to infection by the human T-cell lymphotropic virus type 1 (HTLV-1) virus. About two percent who carry the virus will develop lymphoma. There are 4 subtypes of ATLL: 2 aggressive subtypes, lymphoma-type ATLL and acute ATLL, chronic ATLL, which usually grows more slowly, and smouldering ATLL, which the slowest-growing type.

Enteropathy-type T-cell lymphoma (EATL) is an extremely rare subtype of T-cell lymphoma that appears in the intestines and is strongly associated with celiac disease. There are 2 types of EATL: type 1, classical EATL, and type 2, monomorphic EATL, which is also called monomorphic epitheliotropic intestinal T-cell lymphoma.

Hepatosplenic T-cell lymphoma (HSTL) is a rare extranodal and systemic neoplasm derived from cytotoxic T-cells. HSLT has two types: gamma-delta (γδ) T-cell receptor type and alpha-beta (αβ) type. There is another γδ T-cell lymphoma, primary cutaneous γδ T-cell lymphoma (PCGD-TCL). These lymphomas share an aggressive course and a dismal prognosis with most of the other TCLs.

T-cell lymphoblastic lymphoma (T-LBL) is fast-growing and most often diagnosed in children.

Nasal NK/T-cell Lymphomas are fast-growing lymphomas that typically originate in the lining of the nose or upper airway.

In some embodiments, the T-cell lymphoma is an aggressive T-cell lymphoma.

In some embodiments, the T-cell lymphoma is an indolent T-cell lymphoma.

In some embodiments, the T-cell lymphoma is an immature T-cell lymphoma.

In some embodiments, the T-cell lymphoma is a mature T-cell lymphoma.

In some embodiments, the T-cell lymphoma is nodal T-cell lymphoma.

In some embodiments, the T-cell lymphoma is extranodal T-cell lymphoma.

In some embodiments, the T-cell lymphoma is leukemic T-cell lymphoma.

In some embodiments, the T-cell lymphoma is selected from peripheral T-cell lymphomas, peripheral T-cell lymphomas not otherwise specified, angioimmunoblastic T-cell lymphoma, follicular T-cell lymphoma, anaplastic large cell lymphoma, enteropathy-associated T-cell lymphoma, adult T-cell leukaemia/lymphoma, T-cell leukemia, nasal NK/T-cell lymphoma, hepatosplenic T-cell lymphoma, and cutaneous (skin) T-cell lymphoma.

In some embodiments, the T-cell lymphoma is peripheral T-cell lymphoma.

In some embodiments, the T-cell lymphoma is peripheral T-cell lymphoma not otherwise specified.

In some embodiments, the T-cell lymphoma is angioimmunoblastic T-cell lymphoma.

In some embodiments, the T-cell lymphoma is follicular T-cell lymphoma.

In some embodiments, the T-cell lymphoma is anaplastic large cell lymphoma.

In some embodiments, the T-cell lymphoma is enteropathy-associated T-cell lymphoma.

In some embodiments, the T-cell lymphoma is adult T-cell leukemia/lymphoma.

In some embodiments, the T-cell lymphoma is cutaneous (skin) T-cell lymphoma.

In some embodiments, the T-cell lymphoma is nasal NK/T-cell Lymphoma.

In some embodiments, the T-cell lymphoma is relapsed or refractory T-cell lymphoma or any subtype as described herein. In some embodiments, the T-cell lymphoma is relapsed after or refractory to treatment with a BTK inhibitor, a Bcl-2 inhibitor (e.g., venetoclax), and/or a phosphatidylinositol 3 kinase inhibitor (e.g., tenalisib). In some embodiments, the T-cell lymphoma is relapsed after or refractory to treatment with one or more of alkylating agent, anthracyclines, anti-CD20 antibody, B-cell receptor (BCR) pathway inhibitor, bendamustine, belinostat, bleomycin, bosutinib, brentuximab, carmustine, cytarabine, cyclophosphamide, dacarbazine, doxorubicin, etoposide, gemcitabine, oxiplatin, high-dose steroids, lenalidomide, melphalan, ixazomib, fludarabine, fenretinide, pralatrexate, prednisone, R-CHEP, rituximab, romidepsin, vinblastine, vincristine, and RP-6530. In some embodiments, the T-cell lymphoma is relapsed after or refractory to treatment with one or more of CHOP, brentuximab+rituximab, rituximab+CHOP, gemcitabine+oxiplatin, gemcitabine, high-dose steroids, BEAM, BEAM/R-CHEP, EPOCH, ABVD, lenalidomide, ixazomib, bosutinib, fenretinide, pralatrexate, romidepsin, belinostat, and a PI3K inhibitor, such as tenalisib. In some embodiments, the T-cell lymphoma is relapsed after or refractory to treatment with one or more of belinostat, brentuximab vedotin, pralatrexate, romidepsin, and a PI3K inhibitor.

In some embodiments, cerdulatinib is administered as a second line treatment, third line treatment, fourth line treatment, fifth line treatment, sixth line treatment, seventh line treatment, eighth line treatment, ninth line treatment, tenth line treatment or eleventh line treatment.

In some embodiments, the T-cell lymphoma has not been previously treated with an agent for treating T-cell lymphoma (i.e., treatment naive).

In some embodiments, the T-cell lymphoma is T-cell non-Hodgkin lymphoma. In some embodiments, the T-cell lymphoma is relapsed or refractory T-cell non-Hodgkin lymphoma. In some embodiments, the T-cell lymphoma is peripheral T-cell lymphoma. In some embodiments, the T-cell lymphoma is relapsed or refractory peripheral T-cell lymphoma. In some embodiments, the T-cell lymphoma is a relapsed or refractory subtype of T-cell lymphoma as described herein.

In some embodiments, the patient has a T-cell lymphoma with follicular involvement. In some embodiments, the T-cell lymphoma is a subtype of T-cell lymphoma as described herein with follicular involvement. In some embodiments, the patient has AITL with follicular involvement. In some embodiments, the patient has PTCL-NOS with follicular involvement. In some embodiments, the T-cell lymphoma is relapsed or refractory T-cell lymphoma as described herein with follicular involvement.

In some embodiments, the T-cell lymphoma has at least about 30%, at least about 40%, at least about 50%, at least about 60%, at least about 70%, at least about 80%, or at least about 90% reduction from baseline disease after treatment.

In some embodiments, the patient has at least a stable disease after cerdulatinib treatment. A "stable disease" can refer to a response to the cerdulatinib treatment (alone or in combination with another agent, such as rituximab) where the lymphoma is neither decreasing nor increasing (e.g., substantially) in extent or severity. In some embodiments, the patient has at least a partial response after cerdulatinib treatment. In some embodiments, the patient has a complete response after cerdulatinib treatment. In some embodiments, the patient has a duration of response to cerdulatinib of at least about 2 months, at least about 3 months, at least about 4 months, at least about 5 months, at least about 6 months, at least about 9 months or at least about 12 months. In some embodiments, the patient has at least a partial response with a duration of response to cerdulatinib of at least about 2 months, at least about 3 months, at least about 4 months, at least about 5 months, at least about 6 months, at least about 9 months or at least about 12 months. In some embodiments, the patient has a complete response with a duration of response to cerdulatinib of at least about 2 months, at least about 3 months, at least about 4 months, at least about 5 months, at least about 6 months, at least about 9 months or at least about 12 months. In some embodiments, at least about 30%, at least about 40%, or at least about 50% of the patients being treated with cerdulatinib have at least a stable disease. In some embodiments, at least 30% or at least 40% of the patients being treated with cerdulatinib have at least a partial response.

In some embodiments, the T-cell lymphoma is monomorphic epitheliotropic intestinal T-cell lymphoma. In some embodiments, the monomorphic epitheliotropic intestinal T-cell lymphoma has at least about 30%, at least about 40%, at least about 50%, or at least about 60%, or about 90% reduction in baseline disease after treatment.

In some embodiments, the effective amount of cerdulatinib is a daily dosage of from about 30 mg to about 90 mg. In some embodiments, the effective amount of cerdulatinib is a daily dosage of from about 40 mg, about 50 mg, about 60 mg, or about 70 mg, administered once or twice daily. In some embodiments, the effective amount of cerdulatinib is about 35 mg twice daily. In some embodiments, the effective amount of cerdulatinib is about 30 mg twice daily. In some embodiments, the effective amount of cerdulatinib is about 25 mg twice daily. In some embodiments, the effective amount of cerdulatinib is about 20 mg twice daily. In some embodiments, the effective amount of cerdulatinib is about 30 mg twice daily, and is reduced about 25 mg twice daily. In some embodiments, the effective amount of cerdulatinib is further reduced to about 20 mg twice daily. In some embodiments, the effective amount of cerdulatinib is further reduced to about 15 mg twice daily.

In some embodiments, provided is a method of treating a T-cell lymphoma (e.g., PTCL, PTCL-NOS, ALCL, AITL, CTCL, ATLL, EATL, HSTL, T-LBL, or nasal NK/T-cell lymphoma) in a human patient in need thereof, comprising administering to the patient an effective amount of cerdulatinib or a pharmaceutically acceptable salt, co-crystal or solvate thereof, wherein the effective amount is about 40 mg to about 80 mg of cerdulatinib per day or a corresponding amount of a pharmaceutically acceptable salt of cerdulatinib.

In some embodiments, provided is a method of treating a T-cell lymphoma (e.g., PTCL, PTCL-NOS, ALCL, AITL, CTCL, ATLL, EATL, HSTL, T-LBL, or nasal NK/T-cell lymphoma) in a human patient in need thereof, comprising administering to the patient an effective amount of cerdulatinib or a pharmaceutically acceptable salt, co-crystal or solvate thereof, wherein the effective amount is about 20 mg to about 40 mg of cerdulatinib per dose twice daily or a corresponding amount of a pharmaceutically acceptable salt of cerdulatinib. In some embodiments, the effective amount is about 30 mg of cerdulatinib per dose twice daily or a corresponding amount of a pharmaceutically acceptable salt of cerdulatinib. In some embodiments, the effective amount is about 35 mg of cerdulatinib per dose twice daily or a corresponding amount of a pharmaceutically acceptable salt of cerdulatinib.

In some embodiments, provided is a method of treating a T-cell lymphoma (e.g., PTCL, PTCL-NOS, ALCL, AITL, CTCL, ATLL, EATL, HSTL, T-LBL, or nasal NK/T-cell lymphoma) in a human patient in need thereof, wherein the patient is relapsed after or refractory to treatment with a BTK inhibitor, a Bcl-2 inhibitor, and/or a phosphatidylinositol 3 kinase inhibitor, and the method comprises administering to the patient an effective amount of cerdulatinib or a pharmaceutically acceptable salt, co-crystal or solvate thereof, wherein the effective amount is about 20 mg to about 40 mg of cerdulatinib per dose twice daily or a corresponding amount of a pharmaceutically acceptable salt of cerdulatinib. In some embodiments, the effective amount is about 30 mg of cerdulatinib per dose twice daily or a corresponding amount of a pharmaceutically acceptable salt of cerdulatinib. In some embodiments, the effective amount is about 35 mg of cerdulatinib per dose twice daily or a corresponding amount of a pharmaceutically acceptable salt of cerdulatinib. In some embodiments, the patient is relapsed after or refractory to treatment with one or more of alkylating agent, anthracyclines, anti-CD20 antibody, B-cell receptor (BCR) pathway inhibitor, bendamustine, belinostat, bleomycin, bosutinib, brentuximab, carmustine, cytarabine, cyclophosphamide, dacarbazine, doxorubicin, etoposide, gemcitabine, oxiplatin, high-dose steroids, lenalidomide, melphalan, ixazomib, fludarabine, fenretinide, pralatrexate, prednisone, R-CHEP, rituximab, romidepsin, vinblastine, vincristine, and RP-6530. In some embodiments, the patient is relapsed after or refractory to treatment with one or more of CHOP, brentuximab+rituximab, rituximab+CHOP, gemcitabine+oxiplatin, gemcitabine, high-dose steroids, BEAM, BEAM/R-CHEP, EPOCH, ABVD, lenalidomide, ixazomib, bosutinib, fenretinide, pralatrexate, romidepsin, belinostat, and a PI3K inhibitor, such as tenalisib. In some embodiments, the patient is relapsed after or refractory to treatment with one or more of belinostat, brentuximab vedotin, pralatrexate, romidepsin, and a PI3K inhibitor.

In some embodiments, cerdulatinib is administered with or without food. In some embodiments, cerdulatinib is administered with a proton pump inhibitor, such as esomeprazole, omeprazole, lansoprazole, rabeprazole, dexlansoprazole, or a pharmaceutically acceptable salt thereof.

Treatment of Lymphoma

In some embodiments, provided herein is a method of treating a lymphoma in a human patient in need thereof and wherein the lymphoma expresses one or more of Mcl-1, FOXP1, GAB1, SOCS1, and SOCS3, comprising administering to the patient an effective amount of cerdulatinib or a pharmaceutically acceptable salt, co-crystal or solvate thereof. In some embodiments, lymphoma expresses one or more of Mcl-1, FOXP1, GAB1, SOCS1, and SOCS3 above base line. In some embodiments, base line is the expression level in a human that does not have a lymphoma. In some embodiments, the lymphoma is a B-cell lymphoma. In some embodiments, the lymphoma is a T-cell lymphoma. In some embodiments, the lymphoma is a Hodgkin's lymphoma. In some embodiments, the lymphoma is a non-Hodgkin's lymphoma. In some embodiments, the lymphoma is chronic lymphocytic leukemia (CLL), small lymphocytic lymphoma (SLL), follicular lymphoma (FL), transformed follicular lymphoma (tFL), diffuse large B-cell lymphoma (DLBCL), mantle cell lymphoma (MCL), B-cell non-Hodgkin's lymphoma (NHL), peripheral T-cell lymphoma (PTCL), cutaneous T-cell lymphoma (CTCL), marginal zone lymphoma, mucosa-associated lymphoid tissue (MALT), or Waldenstrom macroglobluinemia (WM).

In some embodiments, provided herein is a method of treating a lymphoma in a human patient in need thereof and having (or known to have) one or more of mutations in FAT4, CCND3, MYOM2, ZMYM3, NOTCH1, KMT2D, TCF3, ARID1A, AXIN1, SYK, JAK1, JAK3, and/or TYK2, comprising administering to the patient an effective amount of cerdulatinib or a pharmaceutically acceptable salt, co-crystal or solvate thereof. In some embodiments, the lymphoma is a B-cell lymphoma. In some embodiments, the lymphoma is a T-cell lymphoma. In some embodiments, the lymphoma is a Hodgkins lymphoma. In some embodiments, the lymphoma is a non-Hodgkins lymphoma. In some embodiments, the lymphoma is chronic lymphocytic leukemia (CLL), small lymphocytic lymphoma (SLL), follicular lymphoma (FL), transformed follicular lymphoma (tFL), diffuse large B-cell lymphoma (DLBCL), mantle cell lymphoma (MCL), B-cell non-Hodgkin's lymphoma (NHL), peripheral T-cell lymphoma (PTCL), cutaneous T-cell lymphoma (CTCL), marginal zone lymphoma, mucosa-associated lymphoid tissue (MALT), or Waldenstrom macroglobluinemia (WM). In some embodiments, the lymphoma is a PTCL, FL, CLL or SLL. In some embodiments, the patient has one or more mutations in FAT4, CCND3, MYOM2, ZMYM3, KMT2D, TCF3, ARID1A, and/or AXIN1. In some embodiments, the patient has one or more mutations in ZMYM3, KMT2D, and FAT4.

In some embodiments, provided herein is a method of treating a follicular lymphoma or in a human patient in need thereof and having (or known to have) one or more of mutations in FAT4, CCND3, MYOM2, ZMYM3, NOTCH1, KMT2D, TCF3, ARID1A, AXIN1, SYK, JAK1, JAK3, and/or TYK2, comprising administering to the patient an effective amount of cerdulatinib or a pharmaceutically acceptable salt, co-crystal or solvate thereof.

In some embodiments, provided herein is a method of treating a follicular lymphoma in a human patient in need thereof and having (or known to have) one or more of mutations in FAT4, CCND3, MYOM2, ZMYM3, KMT2D, TCF3, ARID1A, AXIN1, SYK, JAK1, JAK3, and/or TYK2, comprising administering to the patient an effective amount of cerdulatinib or a pharmaceutically acceptable salt, co-crystal or solvate thereof.

In some embodiments, provided herein is a method of treating a follicular lymphoma in a human patient in need thereof and having (or known to have) one or more of mutations in ZMYM3, KMT2D, FAT4, SYK, JAK1, JAK3, and/or TYK2, comprising administering to the patient an effective amount of cerdulatinib or a pharmaceutically acceptable salt, co-crystal or solvate thereof.

In some embodiments, the patient further has one or more mutations in BCL2, and/or BCL6.

In some embodiments, the follicular lymphoma is relapsed or refractory follicular lymphoma. In some embodiments, the follicular lymphoma is transformed follicular lymphoma. In some embodiments, the follicular lymphoma is relapsed or refractory transformed follicular lymphoma.

In some embodiments, provided herein is a method of treating a lymphoma in a human patient in need thereof and having (or known to have) one or more of mutations in NOTCH1, SETD2, SIGLEC10, SPEN, PCLO, TET2 (e.g., TET2$^{M66L}$), MK167, FAT3, KRAS, REL (e.g., REL$^{I354T}$), HIST1H1E (e.g., HIST1H1E$^{A47V}$), KMT2C, KMT2D, and/or SF3B1, comprising administering to the patient an effective amount of cerdulatinib or a pharmaceutically acceptable salt, co-crystal or solvate thereof. In some embodiments, the lymphoma is a B-cell lymphoma. In some embodiments, the lymphoma is a T-cell lymphoma. In some embodiments, the lymphoma is a Hodgkins lymphoma. In some embodiments, the lymphoma is a non-Hodgkins lymphoma. In some embodiments, the lymphoma is chronic lymphocytic leukemia (CLL), small lymphocytic lymphoma (SLL), follicular lymphoma (FL), transformed follicular lymphoma (tFL), diffuse large B-cell lymphoma (DLBCL), mantle cell lymphoma (MCL), B-cell non-Hodgkin's lymphoma (NHL), peripheral T-cell lymphoma (PTCL), cutaneous T-cell lymphoma (CTCL), marginal zone lymphoma, mucosa-associated lymphoid tissue (MALT), or Waldenstrom macroglobluinemia (WM). In some embodiments, the lymphoma is a PTCL, FL, CLL or SLL. In some embodiments, the patient has one or more mutations in TET2 (e.g., TET2$^{M66L}$, MK167, FAT3, HIST1H1E (e.g., HIST1H1E$^{A47V}$), KMT2C, KMT2D, and/or SF3B1. In some embodiments, the patient has one or more mutations in SYK, JAK1, JAK2, JAK3, TYK2, TP53, STAT (e.g., STAT6$^{S86A}$), A20 (e.g., A20$^{Q150R}$) and/or ATM.

In some embodiments, provided herein is a method of treating chronic lymphocytic leukemia (CLL) or small lymphocytic lymphoma (SLL) in a human patient in need thereof and having (or known to have) one or more of mutations in NOTCH1, SETD2, SIGLEC10, SPEN, PCLO, TET2 (e.g., TET2$^{M66L}$), MK167, FAT3, KRAS, REL (e.g., REL$^{I354T}$), HIST1H1E (e.g., HIST1H1E$^{A47V}$), KMT2C, KMT2D, and/or SF3B1, comprising administering to the patient an effective amount of cerdulatinib or a pharmaceutically acceptable salt, co-crystal or solvate thereof.

In some embodiments, provided herein is a method of treating chronic lymphocytic leukemia (CLL) or small lymphocytic lymphoma (SLL) in a human patient in need thereof and having (or known to have) one or more of mutations in SETD2, SIGLEC10, SPEN, PCLO, TET2 (e.g., TET2$^{M66L}$), MK167, FAT3, KRAS, REL (e.g., REL$^{I354T}$), HIST1H1E (e.g., HIST1H1E$^{A47V}$), KMT2C, KMT2D, and/or SF3B1, comprising administering to the patient an effective amount of cerdulatinib or a pharmaceutically acceptable salt, co-crystal or solvate thereof.

In some embodiments, provided herein is a method of treating chronic lymphocytic leukemia (CLL) or small lymphocytic lymphoma (SLL) in a human patient in need thereof and having (or known to have) one or more of mutations in TET2 (e.g., TET2$^{M66L}$), MK167, FAT3, HIST1H1E (e.g., HIST1H1E$^{A47V}$), KMT2C, KMT2D, and/or SF3B1, comprising administering to the patient an effective amount of cerdulatinib or a pharmaceutically acceptable salt, co-crystal or solvate thereof.

In some embodiments, the patient further has one or more mutations in SYK, JAK1, JAK2, JAK3, TYK2, TP53, STAT (e.g., STAT6$^{S86A}$), A20 (e.g., A20$^{Q150R}$) and/or ATM.

In some embodiments, the patient does not have a mutation in EP300, TP53 and/or BTK. In some embodiments, the patient does not have EP300$^{S697R}$, EP300$^{C1247F}$, TP53$^{N285K}$, TP53$^{R273C}$ and/or BTK$^{C481S}$.

In some embodiments, the CLL or SLL is relapsed or refractory CLL or SLL.

In some embodiments, provided herein is a method of treating a lymphoma (as described herein) in a human patient in need thereof comprising administering to the patient an effective amount of cerdulatinib or a pharmaceutically acceptable salt, co-crystal or solvate thereof and an effective amount of a Mcl-1 inhibitor or a pharmaceutically acceptable salt, co-crystal or solvate thereof.

In some embodiments, the Mcl-1 inhibitor is S63845, MIK665, 483-LM, AZD5991, AMG 176, or a compound described in Structure-Guided Design of a Series of MCL-1 Inhibitors with High Affinity and Selectivity, Bruncko, et al., J. Med. Chem., 2015, 58 (5): 2180-2194, Small Molecule Mcl-1 Inhibitors for the Treatment of Cancer, Belmar, et al., Pharmacol. Ther., 2015, 145:76-84, or Small-Molecule Inhibitors of the Mcl-1 Oncoprotein, Chen, et al., Austin J. Anal. Pharm. Chem., 2014, 1(3), which are hereby incorporated by reference in their entirety.

In some embodiments, the effective amount of the Mcl-1 inhibitor is between about 0.01 and 200 mg/kg. In some embodiments, about 0.01 and 150 mg/kg may be administered. In other embodiments, a dosage of between 0.05 and 100 mg/kg may be administered. The daily dosage is described as a total amount of a Mcl-1 inhibitor administered per day. Daily dosage of a Mcl-1 inhibitor may be between about 0.1 mg and 2,000 mg/day, between about 1 to 2,000 mg/day, between about 1 to 1,000 mg/day, between about 1 to 500 mg/day, between about 10 to 150 mg/day, between about 1 to 100 mg/day, between about between about 1 to 50 mg/day, between about 5 to 100 mg/day, between about 10 to 125 mg/day, between about 10 to 100 mg/day, or between about 5 to 200 mg/day. The daily dosage of a Mcl-1 inhibitor may be administered all in one time (once a day) or in several times, such as two times, three times, four times, five times or more throughout the day.

In some embodiments, provided herein is a method of treating a lymphoma (as described herein) in a human patient in need thereof comprising administering to the patient an effective amount of cerdulatinib or a pharmaceutically acceptable salt, co-crystal or solvate thereof and an effective amount of rituximab (e.g., RITUXAN®, MABTHERA®, ZYTUX®).

In some embodiments, the lymphoma is relapsed or refractory lymphoma. In some embodiments, the lymphoma is B-cell lymphoma. In some embodiments, the B-cell lymphoma is Hodgkin's lymphoma. In some embodiments, the B-cell lymphoma is non-Hodgkin lymphomas. In some embodiments, the lymphoma is follicular lymphoma. In some embodiments, the lymphoma is B-cell chronic lymphocytic leukemia (B-CLL) (also known as chronic lymphoid leukemia (CLL)). In some embodiments, the B-cell lymphoma is small lymphocytic lymphoma (SLL). In some embodiments, the lymphoma is diffuse large B-cell lymphoma (DLBCL or DLBL). In some embodiments, the lymphoma is selected from the group consisting of non-Hodgkin's lymphoma (NHL), Chronic Lymphocytic Leukemia (CLL), Small Lymphocytic Lymphoma (SLL), Follicular Lymphoma (FL), transformed Follicular Lymphoma (tFL), Diffuse Large B-cell Lymphoma (DLBCL), and Mantle Cell Lymphoma (MCL).

In some embodiments, the lymphoma is follicular lymphoma. In some embodiments, the lymphoma is PTCL. In some embodiments, rituximab is co-administered to manage viral infection in the human patient having PTCL.

In some embodiments, the effective amount of rituximab is between about 0.01 and 200 mg/kg. In some embodiments, about 0.01 and 150 mg/kg of rituximab may be administered. In other embodiments, a dosage of between 0.05 and 100 mg/kg of rituximab may be administered. The dosage is described as a total amount of rituximab administered per time period. The dosage of rituximab may be between about 0.1 mg and 2,000 mg/time period, between about 1 to 2,000 mg/time period, between about 1 to 1,000 mg/time period, between about 1 to 500 mg/time period, between about 10 to 150 mg/time period, between about 1 to 100 mg/time period, between about between about 1 to 50 mg/time period, between about 5 to 100 mg/time period, between about 10 to 125 mg/time period, between about 10 to 100 mg/time period, or between about 5 to 200 mg/time period. The dosage of rituximab may be administered all in one time (once per time period) or in several times, such as two times, three times, four times, five times or more throughout the time period. In some embodiments, the time period is, or is about, every day, every two days, every three days, every four days, every five days, every six days, every week, every two weeks, every three weeks, every four weeks, every one month, every two months, every three months, every four months, every five months, every six months, every seven months, every eight months, every nine months, every ten months, every eleven months, every year, or a number or a range between any two of these values.

Dosages

A variety of regimens for administering cerdulatinib may be used. For example, the cerdulatinib may be administered as a single daily dose or as a multiple-dose daily regimen. In some embodiments, the cerdulatinib is administered once, twice, three times or four times a day. In some embodiments, cerdulatinib is administered once daily or twice daily. In some embodiments, cerdulatinib is administered orally.

The specific amount of cerdulatinib described herein refers to the amount of cerdulatinib free base, i.e., the compound of formula I. However, it is understood that a pharmaceutically acceptable salt, co-crystal or solvate of cerdulatinib or a mixture thereof may be administered in an amount that provides the stated amount of cerdulatinib. Examples of pharmaceutically acceptable salts of cerdulatinib include those derived from inorganic or organic acids, such as cerdulatinib acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, edisylate, fumarate, lucoheptanoate, glycerophosphate, hemisulfate, heptanoate, hexanoate, hydrochloride, bis-hydrochloride, hydrobromide, hydroiodide, 2-hydroxyethanesulfonate, lactate, maleate, methanesulfonate, bis-methanesulfonate, 2-naphthalenesulfonate, naphthalene disulfate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulfates, phosphates, nitrates, sulphamates, malonates, salicylates, methylene-bis-b-hydroxynaphthoates, gentisates, isethionates, di-ptoluoyltartrates, ethanesulphonates, cyclohexylsulphamates, quinates, and the like.

Cerdulatinib or a salt thereof can be administered in unsolvated forms as well as solvated forms, including hydrated forms, or form co-crystals with another compound. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate, hemi-hydrate, channel hydrate etc. Some examples of solvents include, but are not limited to, methanol, N,N-dimethylformamide, tetrahydrofuran, dimethylsulfoxide, and water.

In some embodiments, cerdulatinib is administered as a hydrochloride salt (cerdulatinib HCl). In some embodiments, the cerdulatinib HCl is in a crystalline form. In some embodiments, the cerdulatinib HCl is in a crystalline form characterized by an X-ray powder diffractogram comprising peaks at 8.7, 15.9, and 20.0 °2θ, each ±0.2 °2θ, as determined on a diffractometer using Cu-Kα radiation (cerdulatinib HCl Form I). In some embodiments, cerdulatinib HCl Form I is further characterized by one or more peaks at 11.5, 22.5, and 25.5 °2θ, each ±0.2 °2θ. In some embodiments, cerdulatinib HCl Form I is further characterized by a differential scanning calorimetry curve comprising an endotherm with onset at about 288° C.

It has been found that the steady state plasma minimum concentration ($SSC_{min}$) of cerdulatinib is important for achieving better efficacy. A given dosage, such as the dosages described herein, was found to produce different $SSC_{min}$ in different patients, and $SSC_{min}$ needed for achieving better efficacy in different diseases was also found to be different. Accordingly, personalized dosages that achieve sufficient but not excessive $SSC_{min}$ in individual patients tailored for particular diseases will maximize response with minimum side effects.

In some embodiments, the therapeutically effective amount is at least about 5 mg of cerdulatinib per day. In some embodiments, the therapeutically effective amount is at least about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg of cerdulatinib per day. In some embodiments, the therapeutically effective amount is at least about 10, 20, 30, 40, or 50 mg of cerdulatinib per dosage. In some embodiments, the therapeutically effective amount is at least about 15 mg, 20 mg, 25 mg, 30 mg, or 35 mg of cerdulatinib per dosage and is administered twice daily.

In some embodiments, the therapeutically effective amount is no more than about 100 mg, 95 mg, 90 mg, 85 mg, 80 mg, or 75 mg of cerdulatinib per day. In some embodiments, the therapeutically effective amount is no more than about 90 mg, 80 mg, 70 mg, 60 mg, 55 mg or 50 mg of cerdulatinib per dosage. In some embodiments, the therapeutically effective amount is no more than 45 mg, 40 mg, 35 mg, or 30 mg of cerdulatinib per dosage and is administered twice daily.

In some embodiments, the therapeutically effective amount is from about 10 mg to 200 mg, from about 10 mg to 150 mg, from about 25 mg to 150 mg, from about 25 to 120 mg, from 30 mg to 110 mg, from about 50 to 120 mg, from about 30 to 80 mg, from 50 mg to 80 mg, from about 40 to 50 mg or from about 80 to 100 mg of cerdulatinib per day.

In some embodiments, the daily dose of cerdulatinib is about 30 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, or 150 mg.

In some embodiments, from about 30 mg to about 80 mg of cerdulatinib is administered once a day. In some embodiments, the effective amount is about 40 mg, 45 mg, 50 mg, 55 mg, 60 mg, 65 mg, or 70 mg of cerdulatinib administered once daily.

In some embodiments, the effective amount is about 15 mg to about 65 mg, about 25 mg to about 50 mg, about 25 mg to about 40 mg, about 30 mg to about 40 mg or about 40 mg to about 50 mg of cerdulatinib per dosage administered twice daily. In some embodiments, about 25 mg, 30 mg, 35 mg, 40 mg, 45 mg, 50 mg, 55 mg or 60 mg of cerdulatinib is administered twice daily. In some embodiments, about 45 mg of cerdulatinib is administered twice daily. In some embodiments, about 35 mg of cerdulatinib is administered twice daily.

In some embodiments, the effective amount of cerdulatinib is from about 10 mg to about 45 mg daily. In some embodiments, the effective amount of cerdulatinib is from about 15 mg to about 30 mg twice daily. In some embodiments, the effective amount of cerdulatinib is about 15 mg, 20 mg, 25 mg, or 30 mg twice daily.

In some embodiments, cerdulatinib is administered, is administered about, is administered at least, or is administered at most, 5 times, 6 times, 7 times, 8 times, 9 times, 10 times, 20 times, 30 times, 40 times, 50 times, 60 times, 70 times, 80 times, 90 times, 100 times, or a number or a range between any two of these values.

In some embodiments, provided herein is a method of treating a follicular lymphoma or non-Hodgkin's Lymphoma (iNHL) in a human patient in need thereof, comprising administering to the patient an effective amount of cerdulatinib or a pharmaceutically acceptable salt, co-crystal or solvate thereof to achieve and maintain a steady state minimum plasma cerdulatinib concentration of between about 0.05 µM to about 3 µM in the patient. In some embodiments, the method achieves at least a partial response in the treated patient.

In some embodiments, the follicular lymphoma is relapsed or refractory follicular lymphoma. In some embodiments, the follicular lymphoma is transformed follicular lymphoma. In some embodiments, the follicular lymphoma is relapsed or refractory transformed follicular lymphoma. In some embodiments, cerdulatinib or a pharmaceutically acceptable salt, co-crystal or solvate thereof is administered to a FL patient for at least 30 weeks, or at least 40 weeks, or at least 50 weeks.

In some embodiments, provided herein is a method of treating a marginal zone lymphoma, Waldenstrom's macroglobulinemia, chronic lymphocytic leukemia or small lymphocytic lymphoma in a human patient in need thereof, comprising administering to the patient an effective amount of cerdulatinib or a pharmaceutically acceptable salt, co-crystal or solvate thereof to achieve and maintain a steady state minimum plasma cerdulatinib concentration of between about 0.05 µM to about 3 µM in the patient. In some embodiments, the method achieves at least a partial response in the treated patient. In some embodiments, the marginal zone lymphoma is relapsed or refractory marginal zone lymphoma. In some embodiments, the Waldenstrom's macroglobulinemia is relapsed or refractory Waldenstrom's macroglobulinemia. In some embodiments, the chronic lymphocytic leukemia or small lymphocytic lymphoma is relapsed or refractory chronic lymphocytic leukemia or small lymphocytic lymphoma.

In some embodiments, the steady state minimum plasma cerdulatinib concentration achieved and maintained in the human patient is from about 0.7 µM to about 3 µM. In some embodiments, the steady state minimum plasma cerdulatinib concentration achieved and maintained in the human patient is from about 0.05 µM to about 0.5 µM. In some embodiments, the steady state minimum plasma cerdulatinib concentration achieved in the human patient is, is about, is at most, or is at least, 0.001 µM, 0.002 µM, 0.003 µM, 0.004 µM, 0.005 µM, 0.006 µM, 0.007 µM, 0.008 µM, 0.009 µM, 0.01 µM, 0.02 µM, 0.03 µM, 0.04 µM, 0.05 µM, 0.06 µM, 0.07 µM, 0.08 µM, 0.09 µM, 0.1 µM, 0.1 µM, 0.2 µM, 0.3 µM, 0.4 µM, 0.5 µM, 0.6 µM, 0.7 µM, 0.8 µM, 0.9 µM, 1.0 µM, 1.1 µM, 1.2 µM, 1.3 µM, 1.4 µM, 1.5 µM, 1.6 µM, 1.7 µM, 1.8 µM, 1.9 µM, 2.0 µM, 2.1 µM, 2.2 µM, 2.3 µM, 2.4 µM, 2.5 µM, 2.6 µM, 2.7 µM, 2.8 µM, 2.9 µM, 3.0 µM, 3.1 µM, 3.2 µM, 3.3 µM, 3.4 µM, 3.5 µM, 3.6 µM, 3.7 µM, 3.8 µM, 3.9 µM, 4.0 µM, 4.1 µM, 4.2 µM, 4.3 µM, 4.4 µM, 4.5

μM, 4.6 μM, 4.7 μM, 4.8 μM, 4.9 μM, 5.0 μM, or a number or a range between any two of these values.

In some embodiments, the method achieves at least a 30% nodal reduction in the treated patient. In some embodiments, the method achieves at least a 40% nodal reduction in the treated patient. In some embodiments, the method achieves at least a 50% nodal reduction in the treated patient.

Steady state minimum plasma cerdulatinib concentrations may be determined by methods described herein or known in the art. In some embodiments, the patient's steady state minimum plasma cerdulatinib concentration is determined after the patient is administered cerdulatinib for one day, two days, three days, or one week. In some embodiments, the dosage administered to the patient is adjusted so that the steady state minimum plasma cerdulatinib concentration is within the desired ranges.

Patients

In some embodiments of the methods described herein, the patient has resistance to a drug, which is not cerdulatinib. Non-limiting examples of these drugs are an anti-CD20 antibody, a BCL-2 inhibitor, a BTK inhibitor, a P13Kδ inhibitor, rituximab, a platinum-based drug, an antimetabolite, ibrutinib, idelalisib, fludararbine (fludarabine phosphate, FLUDARA®), anthracyclines, a BCR pathway inhibitor, ABT-199 (venetoclax), tofacitinib, or another chemotherapeutic agent used for treating a hematologic cancer. Other non-limiting examples of chemotherapeutic agents include alkylating agents, cytoskeletal disruptors, epothiolones, histone deacetylase inhibitors, inhibitors of topoisomerase I, inhibitors of topoisomerase II, nucleotide analogs and precursor analogs, antibiotics, platinum-based agents, retinoids, vinca alkaloids, or a combination thereof.

In some embodiments of the methods described herein, the patient has resistance to an anti-CD20 antibody, a BCL-2 inhibitor, a BTK inhibitor, a P13Kδ inhibitor, a platinum-based drug, an antimetabolite, ananthracycline, a BCR pathway inhibitor, or another chemotherapeutic agent used for treating a hematologic cancer. In some embodiments, the patient has resistance to a drug selected from the group consisting of ibrutinib, idelalisib, tofacitinib, fludararbine (fludarabine phosphate, FLUDARA®), or ABT-199 (venetoclax). In some embodiments, the patient has resistance to ibrutinib.

In some embodiments, the patient was previously administered a drug for treating a hematological cancer. Non-limiting examples of the drug include an alkylating agent, an anti-CD20 antibody, a BCL-2 inhibitor, a BTK inhibitor, a P13Kδ inhibitor, rituximab, a platinum-based drug, an antimetabolite, ibrutinib, idelalisib, tofacitinib, fludararbine (fludarabine phosphate, FLUDARA®), anthracyclines, a BCR pathway inhibitor, ABT-199 (venetoclax), and other agents used for treating a hematologic cancer.

Other non-limiting examples of chemotherapeutic agents include cytoskeletal disruptors, epothiolones, histone deacetylase inhibitors, inhibitors of topoisomerase I, inhibitors of topoisomerase II, nucleotide analogs and precursor analogs, antibiotics, platinum-based agents, retinoids, vinca alkaloids, or a combination thereof.

In some embodiments, the patient was administered a drug selected from the group consisting of an alkylating agent, an anti-CD20 antibody, a BCL-2 inhibitor, a BTK inhibitor, a P13Kδ inhibitor, a platinum-based drug, an antimetabolite, an anthracycline, a BCR pathway inhibitor, and other agents used for treating a hematologic cancer. In some embodiments, the drug is rituximab, ibrutinib, idelalisib, tofacitinib, fludararbine (fludarabine phosphate, FLUDARA®), or ABT-199 (venetoclax). In some embodiments, the drug is R-CHOP (rituximab; cyclophosphamide; doxorubicin hydrochloride; (vincristine); prednisone). In some embodiments, the drug is R-CVP (rituximab; cyclophosphamide; vincristine; prednisone). In some embodiments, the drug is bevacizumab. In some embodiments, the drug is a combination of fludarabine and rituximab, a combination of bendamustine and rituximab, or a combination of bevacizumab and rituximab.

In certain embodiments, the patient is 60 years or older and relapsed after a first line cancer therapy. In certain embodiments, the patient is 18 years or older and is relapsed or refractory after a second line cancer therapy. In certain embodiments, the patient is 60 years or older and is primary refractory to a first line cancer therapy. In certain embodiments, the patient is 70 years or older and is previously untreated. In certain embodiments, the patient is 70 years or older and is ineligible and/or unlikely to benefit from cancer therapy.

3. Combination Treatments

In one embodiment, the treatment methods can further include administration of an effective amount of another agent, such as a chemotherapeutic agent useful for treating the cancer. In some embodiments, cerdulatinib is co-administered (simultaneously or sequentially) with an effective amount of the another agent or a pharmaceutically acceptable salt, co-crystal or solvate thereof. In some embodiments, the another agent is a chemotherapeutic agent. In some embodiments, the agent that is co-administered with cerdulatinib is a Mcl-1 inhibitor. In some embodiments, the agent that is co-administered with cerdulatinib is rituximab. In some embodiments, the agent is co-administered with cerdulatinib simultaneously or sequentially.

The compounds of the present disclosure can be used in combination with one or more other enzyme/protein/receptor inhibitors for the treatment of diseases, such as cancer. Examples of cancers include solid tumors and liquid tumors, such as blood cancers. For example, the compounds of the present disclosure can be combined with one or more inhibitors of the following kinases for the treatment of cancer: Akt1, Akt2, Akt3, TGFβR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In some embodiments, the compounds of the present disclosure can be combined with one or more of the following inhibitors for the treatment of cancer. Non-limiting examples of inhibitors that can be combined with the compounds of the present disclosure for treatment of cancers include an FGFR inhibitor (FGFR1, FGFR2, FGFR3 or FGFR4, e.g., AZD4547, BAY1187982, ARQ087, BGJ398, BIBF1120, TK1258, lucitanib, dovitinib, TAS-120, JNJ-42756493, Debio1347, INCB54828, INCB62079 and INCB63904), a JAK inhibitor (JAK1 and/or JAK2, e.g., ruxolitinib, baricitinib or INCB39110), an IDO inhibitor (e.g., epacadostat and NLG919), an LSD1 inhibitor (e.g., GSK2979552, INCB59872 and INCB60003), a TDO inhibitor, a PI3K-delta inhibitor (e.g., INCB50797 and INCB50465), a PI3K-gamma inhibitor such as a PI3K-gamma selective inhibitor, a CSF1R inhibitor (e.g., PLX3397 and LY3022855), a TAM receptor tyrosine kinases (Tyro-3, Axl, and Mer), an angiogenesis inhibitor, an interleukin receptor inhibitor, bromo and extra terminal family members inhibitors (for example, bromodomain inhibitors or BET inhibitors such as OTX015, CPI-0610, INCB54329 and INCB57643) and an adenosine receptor antagonist or combinations thereof. Inhibitors of HDAC such as panobinostat and vorinostat. Inhibitors of c-Met such as onartumzumab, tivantnib, and INC-280. Inhibitors of BTK such as ibrutinib. Inhibitors of mTOR such as rapamycin, sirolimus, temsirolimus, and everolimus. Inhibitors of Raf, such as vemurafenib and dabrafenib. Inhibitors of MEK such as trametinib, selumetinib and GDC-0973. Inhibitors of Hsp90 (e.g., tanespimycin), cyclin dependent kinases (e.g., palbociclib), PARP (e.g., olaparib) and Pim kinases (LGH447, INCB053914 and SGI-1776) can also be combined with compounds of the present disclosure.

Compounds of the present disclosure can be used in combination with one or more immune checkpoint inhibitors. Exemplary immune checkpoint inhibitors include inhibitors against immune checkpoint molecules such as CD20, CD27, CD28, CD39, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab. In some embodiments, the anti PD-1 antibody is SHR-1210.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of CSF1R, e.g., an anti-CSF1R antibody. In some embodiments, the anti-CSF1R antibody is IMC-CS4 or RG7155.

In some embodiments, the inhibitor of an immune checkpoint molecule is an inhibitor of LAG3, e.g., an anti-LAG3 antibody. In some embodiments, the anti-LAG3 antibody is BMS-986016, LAG525, IMP321 or GSK2831781.

In some embodiments, the inhibitor of an immune checkpoint molecule is an inhibitor of GITR, e.g., an anti-GITR antibody. In some embodiments, the anti-GITR antibody is TRX518, MK-4166, MK1248, BMS-986156, MEDI1873 or GWN323.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562, MEDI6469, MOXR0916, PF-04518600 or GSK3174998. In some embodiments, the OX40L fusion protein is MEDI6383.

In some embodiments, the inhibitor of an immune checkpoint molecule is an inhibitor of TIM3, e.g., an anti-TIM3 antibody. In some embodiments, the anti-TIM3 antibody is MBG-453.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the compounds of the invention can be used in combination with one or more metabolic enzyme inhibitors. In some embodiments, the metabolic enzyme inhibitor is an inhibitor of IDO1, TDO, or arginase. Examples of IDO1 inhibitors include epacadostat and NGL919. An example of an arginase inhibitor is CB-1158.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include bendamustine, nitrogen mustards, ethylenimine derivatives, alkyl sulfonates, nitrosoureas and triazenes, uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, abiraterone, afatinib, aflibercept, aldesleukin, alemtuzumab, alitretinoin, allopurinol, altretamine, anastrozole, arsenic trioxide, asparaginase, axitinib, azacitidine, bevacizumab, bexarotene, baricitinib, bicalutamide, bleomycin, bortezombi, bortezomib, brivanib, buparlisib, busulfan intravenous, busulfan oral, calusterone, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, docetaxel, doxorubicin, droloxafine, dromostanolone propionate, eculizumab, enzalutamide, epidophyllotoxin, epirubicin, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, nofetumomab, oserelin, oxaliplatin, paclitaxel, pamidronate, panitumumab, pazopanib, pegaspargase, pegfilgrastim, pemetrexed disodium, pentostatin, pilaralisib, pipobroman, plicamycin, ponatinib, prednisone, procarbazine, quinacrine, rasburicase, regorafenib, reloxafine, rituximab, sorafenib, streptozocin, sunitinib, sunitinib maleate, tamoxifen, tegafur, temozolomide, teniposide, testolactone, thalidomide, thioguanine, thiotepa, topotecan, toremifene, tositumomab, trastuzumab, tretinoin, triptorelin, uracil mustard, valrubicin, vandetanib, vinblastine, vincristine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab or tremelimumab), 4-1BB, antibodies to PD-1 and PD-L1, or antibodies to cytokines (IL-10, TGF-.beta., etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk and SGK.

Other anti-cancer agents also include those that block immune cell migration such as antagonists to chemokine receptors, including CCR2 and CCR4.

The compounds of the present disclosure can further be used in combination with one or more anti-inflammatory agents, steroids, immunosuppressants or therapeutic antibodies.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

The compounds of the present disclosure can be used in combination with bone marrow transplant for the treatment of a variety of tumors of hematopoietic origin.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4D and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimid-inedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

When more than one pharmaceutical agent is administered to a patient, they can be administered simultaneously, separately, sequentially, or in combination (e.g., for more than two agents). In some embodiments, the another agent can be selected from one of the classes detailed below.

Polyfunctional alkylating agents, exemplified by cyclophosphamide (cytoxan), mechlorethamine, melphalan (alkeran), chlorambucil (leukeran), thiopeta (thioplex), busulfan (myleran);

Alkylating drugs, exemplified by procarbazine (matulane), dacarbazine (dtic), altretamine (hexalen), clorambucil, cisplatin (platinol), carboplatin, ifosafamide, oxaliplatin;

Antimetabolites, exemplified by methotrexate (MTX), 6-thiopurines (mercaptopurine [6-mp], thioguanine [6-TG]), mercaptopurine (purinethol), thioguanine, fludarabine phosphate, cladribine: (leustatin), pentostatin, fluoruracil (5-Fu), cytarabine (ara-C), azacitidine;

Plant alkaloids, terpenoids and topoisomerase inhibitors, exemplified by vinblastine (velban), vincristine (oncovin), vindesine, vinorelbine, podophyllotoxins (etoposide (VP-16) and teniposide (VM-26)), camptothecins (topotecan and irinotecan), taxanes such as paclitaxel (taxol) and docetaxel (taxotere);

Antibiotics, exemplified by doxorubicin (adriamycin, rubex, doxil), daunorubicin, idarubicin, dactinomycin (cosmegen), plicamycin (mithramycin), mitomycin: (mutamycin), bleomycin (blenoxane);

Hormonal agents, exemplified by estrogen and androgen inhibitors (tamoxifen and flutamide), gonadotropin-releasing hormone agonists (leuprolide and goserelin (Zoladex)), aromatase inhibitors (aminoglutethimide and anastrozole (arimidex));

Miscellaneous Anticancer Drugs, exemplified by amsacrine, asparaginase (El-spar), hydroxyurea, mitoxantrone (novantrone), mitotane (lysodren), retinoic acid derivatives, bone marrow growth factors (sargramostim and filgrastim), amifostine;

Agents disrupting folate metabolism, e.g., pemetrexed;

DNA hypomethylating agents, e.g., azacitidine, decitabine;

Poly(adenosine diphosphate [ADP]-ribose) polymerase (PARP) pathway inhibitors, such as iniparib, olaparib, veliparib;

PI3K/Akt/mTOR pathway inhibitors, e.g., everolimus;

Histone deacetylase (HDAC) inhibitors, e.g., vorinostat, entinostat (SNDX-275), mocetinostat (MGCD0103), panobinostat (LBH589), romidepsin, valproic acid;

Cyclin-dependent kinase (CDK) inhibitors, e.g., flavopiridol, olomoucine, roscovitine, kenpaullone, AG-024322 (Pfizer), fascaplysin, ryuvidine, purvalanol A, NU2058, BML-259, SU 9516, PD-0332991, P276-00;

Heat shock protein (HSP90) inhibitors, e.g., geldanamycin, tanespimycin, alvespimycin, radicicol, deguelin, BIIB021;

Murine double minute 2 (MDM2) inhibitors, e.g., cis-imidazoline, benzodiazepinedione, spiro-oxindoles, isoquinolinone, thiophene, 5-deazaflavin, tryptamine;

Anaplastic lymphoma kinase (ALK) inhibitors, e.g., aminopyridine, diaminopyrimidine, pyridoisoquinoline, pyrrolopyrazole, indolocarbazole, pyrrolopyrimidine, dianilinopyrimidine;

Poly [ADPribose] polymerase (PARP) inhibitors, illustrated by benzamide, phthalazinone, tricyclic indole, benzimidazole, indazole, pyrrolocarbazole, phthalazinone, or isoindolinone;

A platinum-based drug, an antimetabolite, a BCL-2 inhibitor, a BTK inhibitor, a P13Kδ inhibitor, an anti-CD20 antibody, such as rituximab, obinutuzumab, ibritumomab tiuxetan, tositumomab, or veltuzumab, or a combination thereof; or ABT-199 (Venetoclax), rituximab (RITUXAN®, MABTHERA®, ZYTUX®), ibrutinib (IMBRUVICA®), idelalisib (ZYDELIG®), tofacitinib, or a combination thereof.

In some embodiments, the other chemotherapeutic agent is a p90RSK inhibitor, such as those described in Cohen et al., "A clickable inhibitor reveals context-dependent auto-activation of p90 RSK," Nat Chem Biol. 2007 Mar.; 3(3): 156-160, and U.S. Pat. No. 7,605,241. In one aspect, the p90RSK inhibitor is one or more of dexamethasone, melphalan, doxorubicin, bortezomib, lenalidomide, prednisone, carmustine, etoposide, cisplatin, vincristine, cyclophosphamide, BI-D1870, and thalidomide.

In some embodiments, cerdulatinib, or a pharmaceutically acceptable salt, co-crystal or solvate thereof, can be administered with a proton pump inhibitor, such as esomaprazole, omeprazole, lansoprazole, rabeprazole, dexlansoprazole, or a pharmaceutically acceptable salt thereof.

The specific amount of the agent co-administered with cerdulatinib described herein refers to the amount of the co-administered agent as a free base. However, it is understood that a pharmaceutically acceptable salt, co-crystal or solvate of the agent co-administered with cerdulatinib or a mixture thereof may be administered in an amount that provides the stated amount of the co-administered agent. Examples of pharmaceutically acceptable salts of the agent co-administered with cerdulatinib include those derived from inorganic or organic acids, such as acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, edisylate, fumarate, lucoheptanoate, glycerophosphate, hemisulfate, heptanoate, hexanoate, hydrochloride, bis-hydrochloride, hydrobromide, hydroiodide, 2-hydroxyethanesulfonate, lactate, maleate, methanesulfonate, bis-methanesulfonate, 2-naphthalenesulfonate, naphthalene disulfate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulfates, phosphates, nitrates, sulphamates, malonates, salicylates, methylene-bis-b-hydroxynaphthoates, gentisates, isethionates, di-ptoluoyltartrates, ethanesulphonates, cyclohexylsulphamates, quinates, and the like.

The co-administered agent or a salt thereof can be administered in unsolvated forms as well as solvated forms, including hydrated forms, or form co-crystals with another compound. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate, hemi-hydrate, channel hydrate etc. Some examples of solvents include, but are not limited to, methanol, N,N-dimethylformamide, tetrahydrofuran, dimethylsulfoxide, and water.

In some embodiments, the effective amount of the agent co-administered with cerdulatinib (e.g., rituximab) is at least about 5 mg per day. In some embodiments, the effective amount of the agent co-administered with cerdulatinib is at least about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg per day. In some embodiments, the effective amount of the agent co-administered with cerdulatinib is at least about 10, 20, 30, 40, or 50 mg per dosage. In some embodiments, the effective amount of the agent co-administered with cerdulatinib is at least about 15 mg, 20 mg, 25 mg, 30 mg, or 35 mg per dosage and is administered twice daily.

In some embodiments, the effective amount of the agent co-administered with cerdulatinib is no more than about 100 mg, 95 mg, 90 mg, 85 mg, 80 mg, or 75 mg of per day. In some embodiments, the effective amount of the agent co-administered with cerdulatinib is no more than about 90 mg, 80 mg, 70 mg, 60 mg, 55 mg or 50 mg per dosage. In some embodiments, the effective amount of the agent co-administered with cerdulatinib is no more than 45 mg, 40 mg, 35 mg, or 30 mg per dosage and is administered twice daily.

In some embodiments, the effective amount of the agent co-administered with cerdulatinib is from about 10 mg to 200 mg, from about 10 mg to 150 mg, from about 25 mg to 150 mg, from about 25 to 120 mg, from 30 mg to 110 mg, from about 50 to 120 mg, from about 30 to 80 mg, from 50 mg to 80 mg, from about 40 to 50 mg or from about 80 to 100 mg per day.

In some embodiments, the daily dose of the agent co-administered with cerdulatinib is about 30 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, or 150 mg.

In some embodiments, from about 30 mg to about 80 mg of the agent is co-administered with cerdulatinib once a day. In some embodiments, the effective amount is about 40 mg, 45 mg, 50 mg, 55 mg, 60 mg, 65 mg, or 70 mg of the agent co-administered with cerdulatinib once daily.

In some embodiments, the effective amount of the agent co-administered with cerdulatinib is about 15 mg to about 65 mg, about 25 mg to about 50 mg, about 25 mg to about 40 mg, about 30 mg to about 40 mg or about 40 mg to about 50 mg per dosage administered twice daily. In some embodiments, about 25 mg, 30 mg, 35 mg, 40 mg, 45 mg, 50 mg, 55 mg or 60 mg of the agent is co-administered with cerdulatinib twice daily. In some embodiments, about 45 mg of the agent is co-administered with cerdulatinib twice daily. In some embodiments, about 35 mg of the agent co-administered with twice daily.

In some embodiments, the effective amount of the agent co-administered with cerdulatinib is a daily dosage of from about 30 mg to about 90 mg. In some embodiments, the effective amount of the agent co-administered with cerdulatinib is a daily dosage of from about 40 mg, about 50 mg, about 60 mg, or about 70 mg, administered once or twice daily. In some embodiments, the effective amount of the agent co-administered with cerdulatinib is about 35 mg twice daily. In some embodiments, the effective amount of the agent co-administered with cerdulatinib is about 30 mg twice daily. In some embodiments, the effective amount of the agent co-administered with cerdulatinib is about 25 mg twice daily. In some embodiments, the effective amount of the agent co-administered with cerdulatinib is about 20 mg twice daily. In some embodiments, the effective amount of the agent co-administered with cerdulatinib is about 30 mg twice daily, and is reduced about 25 mg twice daily. In some embodiments, the effective amount of the agent co-administered with cerdulatinib is further reduced to about 20 mg twice daily. In some embodiments, the effective amount of the agent co-administered with cerdulatinib is further reduced to about 15 mg twice daily.

In some embodiments, the effective amount of the agent co-administered with cerdulatinib is between about 0.01 and 200 mg/kg. In some embodiments, about 0.01 and 150 mg/kg of agent may be co-administered with cerdulatinib. In other embodiments, a dosage of between 0.05 and 100 mg/kg of rituximab may be co-administered with cerdulatinib. The dosage is described as a total amount of rituximab administered per time period. The dosage of the agent co-administered with cerdulatinib may be between about 0.1 mg and 2,000 mg/time period, between about 1 to 2,000 mg/time period, between about 1 to 1,000 mg/time period, between about 1 to 500 mg/time period, between about 10 to 150 mg/time period, between about 1 to 100 mg/time period, between about between about 1 to 50 mg/time period, between about 5 to 100 mg/time period, between about 10 to 125 mg/time period, between about 10 to 100 mg/time period, or between about 5 to 200 mg/time period. The dosage of rituximab may be administered all in one time (once per time period) or in several times, such as two times, three times, four times, five times or more throughout the time period. In some embodiments, the time period is, or is about, every week, every two weeks, every three weeks, every four weeks, every one month, every two months, every three months, every four months, every five months, every six months, every seven months, every eight months, every nine months, every ten months, every eleven months, every year, or a number or a range between any two of these values.

In some embodiments, rituximab is co-administered per its package insert. In some embodiments, rituximab is administered by infusion, such as by intravenous injection. In some embodiments, the effective amount of rituximab is 375 mg/m$^2$, for example, to treat a patient with Non-Hodgkin's Lymphoma (NHL). In some embodiments, the NHL is relapsed or refractory, low grade or follicular, CD20-positive B-cell NHL. In some embodiments, the NHL is previously untreated follicular, CD20-positive, B-cell NHL, for example, in combination with first line chemotherapy. In some embodiments, the patient has achieved a complete or partial response to rituximab, for example, in combination with chemotherapy, and rituximab, for example, in combination with cerdulatinib, can be used for maintenance therapy. In some embodiments, the NHL is non-progressing (including stable disease), low-grade, CD20-positive, B-cell NHL, for example, after first-line cyclophosphamide, vincristine, and prednisone (CVP) chemotherapy. In some embodiments, the NHL is previously untreated diffuse large B-cell, CD20-positive NHL, for example, in combination with (cyclophosphamide, doxorubicin, vincristine, and prednisone) (CHOP) or other anthracycline-based chemotherapy regimens. In some embodiments, the effective amount of rituximab is 375 mg/m$^2$ the first cycle and 500 mg/m$^2$ in cycles 2-6 in combination with fludarabine and cyclophosphamide (FC), administered every 28 days, for example, to treat a patient with Chronic Lymphocytic Leukemia (CLL). In some embodiments, the effective amount of rituximab is 250 mg/m$^2$, for example, in combination with ibritumomab tiuxetan. In some embodiments, the effective amount of rituximab, for example in combination with methotrexate, is two-1000 mg intravenous infusions separated by 2 weeks (one course) every 24 weeks or based on clinical evaluation, but not sooner than every 16 weeks. In some embodiments, the effective amount of rituximab is 375 mg/m$^2$ (for example in combination with gluoccorticoids) once weekly for 4 weeks, and, for example, to treat a patient who has achieved disease control, two 500 mg intravenous infusions separated by two weeks, followed by a 500 mg intravenous infusion every 6 months thereafter based on clinical evaluation. In some embodiments, the effective amount of rituximab is two-1000 mg intravenous infusions separated by 2 weeks in combination with a tapering course of glucocorticoids, then a 500 mg intravenous infusion at Month 12 and every 6 months thereafter or based on clinical evaluation, and upon relapse is a 1000 mg intravenous infusion, with subsequent infusions no sooner than 16 weeks after the previous infusion.

In some embodiments, rituximab is administered in the dosage forms and strengths of 100 mg/10 mL (10 mg/mL) and 500 mg/50 mL (10 mg/mL) solution, for example, in single-dose vials.

In some embodiments, rituximab is administered at a dose of 375 mg/m$^2$ as an intravenous infusion. In some embodiments, rituximab is administered once weekly for 4 or 8 doses, for example, to treat a patient with Relapsed or Refractory, Low-Grade or Follicular, CD20-Positive, B-Cell NHL. In some embodiments, rituximab is administered once weekly for 4 doses, for example, to treat a patient with Relapsed or Refractory, Low-Grade or Follicular, CD20-

Positive, B-Cell NHL. In some embodiments, rituximab is administered on Day 1 of each cycle of chemotherapy, for up to 8 doses, for example, to treat a patient with Previously Untreated, Follicular, CD20-Positive, B-Cell NHL. In some embodiments, if complete or partial response is achieved, rituximab maintenance is initiated eight weeks following completion of rituximab administering, for example, in combination with chemotherapy. In some embodiments, rituximab maintenance includes administering rituximab with cerdulatinib every 8 weeks for 12 doses. In some embodiments, rituximab is administered once weekly for 4 doses at 6-month intervals to a maximum of 16 doses, for example, to treat a patient with Non-progressing, Low-Grade, CD20-Positive, B-Cell NHL (e.g., after first-line CVP chemotherapy). In some embodiments, rituximab is administered on Day 1 of each cycle of chemotherapy for up to 8 infusions, for example, to treat a patient with Diffuse Large B-Cell NHL.

In some embodiments, rituximab is administered at a dose of 375 mg/m$^2$ the day prior to the initiation of FC chemotherapy, then 500 mg/m$^2$ on Day 1 of cycles 2-6 (every 28 days), for example, to treat a patient with Chronic Lymphocytic Leukemia (CLL).

In some embodiments, rituximab is administered at a dose of 250 mg/m$^2$, for example, to treat a patient with NHL. In some embodiments, rituximab is administered 4 hours prior to the administration of Indium-111-(In-111-) Zevalin and within 4 hours prior to the administration of Yttrium-90-(Y-90-) Zevalin. IN some embodiments, rituximab and In-111-Zevalin are administered 7-9 days prior to RITUXAN and Y-90-Zevalin are administered.

In some embodiments, the effective amount of rituximab is an amount determined by a medical practitioner for treatment of the disease or indication.

In some embodiments, the effective amount of rituximab (e.g., for the dose of the first cycle and for the doses of the subsequent cycles) is, or is about, 100 mg/m$^2$, 110 mg/m$^2$, 120 mg/m$^2$, 130 mg/m$^2$, 140 mg/m$^2$, 150 mg/m$^2$, 160 mg/m$^2$, 170 mg/m$^2$, 180 mg/m$^2$, 190 mg/m$^2$, 200 mg/m$^2$, 210 mg/m$^2$, 220 mg/m$^2$, 230 mg/m$^2$, 240 mg/m$^2$, 250 mg/m$^2$, 260 mg/m$^2$, 270 mg/m$^2$, 280 mg/m$^2$, 290 mg/m$^2$, 300 mg/m$^2$, 310 mg/m$^2$, 320 mg/m$^2$, 330 mg/m$^2$, 340 mg/m$^2$, 350 mg/m$^2$, 360 mg/m$^2$, 370 mg/m$^2$, 375 mg/m$^2$, 380 mg/m$^2$, 390 mg/m$^2$, 400 mg/m$^2$, 410 mg/m$^2$, 420 mg/m$^2$, 430 mg/m$^2$, 440 mg/m$^2$, 450 mg/m$^2$, 460 mg/m$^2$, 470 mg/m$^2$, 480 mg/m$^2$, 490 mg/m$^2$, 500 mg/m$^2$, 510 mg/m$^2$, 520 mg/m$^2$, 530 mg/m$^2$, 540 mg/m$^2$, 550 mg/m$^2$, 560 mg/m$^2$, 570 mg/m$^2$, 580 mg/m$^2$, 590 mg/m$^2$, 600 mg/m$^2$, 610 mg/m$^2$, 620 mg/m$^2$, 630 mg/m$^2$, 640 mg/m$^2$, 650 mg/m$^2$, 660 mg/m$^2$, 670 mg/m$^2$, 680 mg/m$^2$, 690 mg/m$^2$, 700 mg/m$^2$, 710 mg/m$^2$, 720 mg/m$^2$, 730 mg/m$^2$, 740 mg/m$^2$, 750 mg/m$^2$, 760 mg/m$^2$, 770 mg/m$^2$, 780 mg/m$^2$, 790 mg/m$^2$, 800 mg/m$^2$, 810 mg/m$^2$, 820 mg/m$^2$, 830 mg/m$^2$, 840 mg/m$^2$, 850 mg/m$^2$, 860 mg/m$^2$, 870 mg/m$^2$, 880 mg/m$^2$, 890 mg/m$^2$, 900 mg/m$^2$, 910 mg/m$^2$, 920 mg/m$^2$, 930 mg/m$^2$, 940 mg/m$^2$, 950 mg/m$^2$, 960 mg/m$^2$, 970 mg/m$^2$, 980 mg/m$^2$, 990 mg/m$^2$, 1000 mg/m$^2$, or a number or a range between any two of these values, per dose or time period for a number of times or cycles.

In some embodiments, the effective amount of rituximab per dose is from about 50 mg to about 1000 mg every three to five weeks up to five to seven times. In some embodiments, the effective amount of rituximab is from about 100 mg to about 500 mg every three to five weeks up to six times. In some embodiments, the effective amount of rituximab is from about 100 mg to about 500 mg every 28 days up to six times. In some embodiments, the effective amount of rituximab (e.g., for the dose of the first cycle and for the doses of the subsequent cycles) is, or is about, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg 1000 mg, or a number or a range between any two of these values, per dose or time period for a number of times or cycles.

In some embodiments, the effective amount of rituximab is once weekly for about 4 or 8 doses. In some embodiments, the effective amount of rituximab is once weekly for about 4 doses. In some embodiments, the time period between two consecutive doses is, or is about, every day, every two days, every three days, every four days, every five days, every six days, every week, every two weeks, every three weeks, every four weeks, every one month, every two months, every three months, every four months, every five months, every six months, every seven months, every eight months, every nine months, every ten months, every eleven months, every twelve months, or a number or a range between any two of these values. In some embodiments, the number of times or cycles is, is about, or is at most, 2, 3, 4, 5, 6, 7, 8, 9, 10, 11, 12, 13, 14, 15, 16, 17, 18, 19, 20, or a number or a range between any two of these values.

In some embodiments, the dose for the first cycle and the doses of the subsequent cycles are identical. In some embodiments, the dose for the first cycle and the doses of the subsequent cycles are different.

In some embodiments, the effective amount of rituximab includes two initial doses separated by about two weeks and subsequent doses every six months thereafter. In some embodiments, the effective amount of rituximab includes two initial doses separated by about two weeks and subsequent doses at month 12 and every six months thereafter. In some embodiments, the effective amount of rituximab includes a number of initial doses, such as 1 dose, 2 doses, 3 doses, 4 dose, 5 doses, 6 doses, 7 doses, 8 doses, 9 doses, or 10 doses. In some embodiments, the two consecutive initial doses are separated by, or by about, 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, or a number or a range between any two of these values. In some embodiments, subsequent doses are administered starting, or starting about, 6 months, 7 months, 8 months, 9 months, 10 months, 11 months, 12 months, 13 months, 14 months, 15 months, 16 months, 17 months, 18 months, or a number or a range between any two of these values. In some embodiments, the subsequent doses are administered, or administered about, every 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, or a number or a range between any two of these values. In some embodiments, the number of subsequent doses is, or is about, 1 dose, 2 doses, 3 doses, 4 doses, 5 doses, 6 doses, 7 doses, 8 doses, 9 doses, 10 doses, 11 doses, 12 doses, 13 doses, 14 doses, 15 doses, 16 doses, 17 doses, 19 doses, 19 doses, 20 doses, or a number or a range between of these two values.

In some embodiments, rituximab (e.g., in combination with cerdulatinib) is used for maintenance after complete or partial response begins about eight weeks following completion of a rituximab product. In some embodiments, rituximab used for maintenance is administered every 8 weeks for 12 doses. In some embodiments, rituximab is used for maintenance after complete or partial response following, or following about, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, or a number or a range between of these two values, completion of a rituximab product. In some embodiments, rituximab used for maintenance is administered, or administered about, every 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, or a number or a range between of these two values. In some embodiments, rituximab used for maintenance is administered, or administered about, 1 dose, 2 doses, 3 doses, 4 doses, 5 doses, 6 doses, 7 doses, 8 doses, 9 doses, 10 doses, 11 doses, 12 doses, 13 doses, 14 doses, 15 doses, 16 doses, 17 doses, 19 doses, 19 doses, 20 doses, or a number or a range between of these two values.

In some embodiments, the effective amount of rituximab is co-administered with cerdulatinib at from about 100 mg/10 mL to about 500 mg/50 mL. In some embodiments, the effective amount of rituximab is co-administered with cerdulatinib at from about 100 mg/10 mL to about 200 mg/20 mL. In some embodiments, the effective amount of rituximab is co-administered with cerdulatinib at from about 200 mg/20 mL to about 300 mg/30 mL. In some embodiments, the effective amount of rituximab is co-administered with cerdulatinib at from about 300 mg/30 mL to about 400 mg/40 mL. In some embodiments, the effective amount of rituximab is co-administered with cerdulatinib at from about 400 mg/40 mL to about 500 mg/50 mL.

In some embodiments, the effective amount of rituximab is co-administered with cerdulatinib in a concentration of about 5 mg/mL. In some embodiments, the effective amount of rituximab is co-administered with cerdulatinib in a concentration of about 10 mg/mL. In some embodiments, the effective amount of rituximab is co-administered with cerdulatinib in a concentration of about 15 mg/mL. In some embodiments, the effective amount of rituximab is co-administered with cerdulatinib in a concentration of from about 5 mg/mL to about 15 mg/mL. In some embodiments, the effective amount of rituximab is co-administered with cerdulatinib in a concentration of from about 5 mg/mL to about 10 mg/mL. In some embodiments, the effective amount of rituximab is co-administered with cerdulatinib in a concentration of from about 10 mg/mL to about 15 mg/mL. In some embodiments, the effective amount of rituximab is co-administered in a concentration of from about 15 mg/mL to about 20 mg/mL. In some embodiments, the effective amount of rituximab (or another agent) is co-administered with cerdulatinib in a concentration of about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL. 11 mg/mL, 12 mg/mL, 13 mg/mL, 14 mg/mL, 15 mg/mL, 16 mg/mL, 17 mg/mL, 18 mg/mL, 19 mg/mL, 20 mg/mL. 21 mg/mL, 22 mg/mL, 23 mg/mL, 24 mg/mL, 25 mg/mL, 26 mg/mL, 27 mg/mL, 28 mg/mL, 29 mg/mL, 30 mg/mL. or a number or a range between any two of these values.

In some embodiments is provided a composition comprising cerdulatinib and the agent co-administered with cerdulatinib (e.g., rituximab). In some embodiments, the molar ratio of cerdulatinib to the co-administered agent is about 300:1 to about 3:1. In some embodiments, the composition comprises cerdulatinib and the agent co-administered with cerdulatinib in a molar ratio of about 9:1 to about 1:9. In some embodiments, the composition comprises cerdulatinib and the agent co-administered with cerdulatinib in a molar ratio of about 2:1 to about 1:2. In some embodiments, the composition comprises cerdulatinib and the agent co-administered with cerdulatinib in a molar ratio of about 2:1 to about 1:5. In some embodiments, the composition comprises cerdulatinib and the agent co-administered with cerdulatinib in a molar ratio of about 1:1. In some embodiments, the composition comprises cerdulatinib and the agent co-administered with cerdulatinib in a molar ratio of about 1:1, about 1:2, about 1:9, about 2:1, or about 9:1. In some embodiments, the composition comprises cerdulatinib and the agent co-administered with cerdulatinib in a molar ratio of, of about, of at least, or of at most, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, or a number or a range between any two of these values. In some embodiments, the composition comprises cerdulatinib and the agent co-administered with cerdulatinib in a molar ratio of, of about, of at least, or of at most, 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, or a number or a range between any two of these values.

In some embodiments, the effective amount of the agent co-administered with cerdulatinib (e.g., rituximab), whether for the dose of the first cycle and for the doses of the subsequent cycles, is, or is about, 100 mg/m$^2$, 110 mg/m$^2$, 120 mg/m$^2$, 130 mg/m$^2$, 140 mg/m$^2$, 150 mg/m$^2$, 160 mg/m$^2$, 170 mg/m$^2$, 180 mg/m$^2$, 190 mg/m$^2$, 200 mg/m$^2$, 210 mg/m$^2$, 220 mg/m$^2$, 230 mg/m$^2$, 240 mg/m$^2$, 250 mg/m$^2$, 260 mg/m$^2$, 270 mg/m$^2$, 280 mg/m$^2$, 290 mg/m$^2$, 300 mg/m$^2$, 310 mg/m$^2$, 320 mg/m$^2$, 330 mg/m$^2$, 340 mg/m$^2$, 350 mg/m$^2$, 360 mg/m$^2$, 370 mg/m$^2$, 375 mg/m$^2$, 380 mg/m$^2$, 390 mg/m$^2$, 400 mg/m$^2$, 410 mg/m$^2$, 420 mg/m$^2$, 430 mg/m$^2$, 440 mg/m$^2$, 450 mg/m$^2$, 460 mg/m$^2$, 470 mg/m$^2$, 480 mg/m$^2$, 490 mg/m$^2$, 500 mg/m$^2$, 510 mg/m$^2$, 520 mg/m$^2$, 530 mg/m$^2$, 540 mg/m$^2$, 550 mg/m$^2$, 560 mg/m$^2$, 570 mg/m$^2$, 580 mg/m$^2$, 590 mg/m$^2$, 600 mg/m$^2$, 610 mg/m$^2$, 620 mg/m$^2$, 630 mg/m$^2$, 640 mg/m$^2$, 650 mg/m$^2$, 660 mg/m$^2$, 670 mg/m$^2$, 680 mg/m$^2$, 690 mg/m$^2$, 700 mg/m$^2$, 710 mg/m$^2$, 720 mg/m$^2$, 730 mg/m$^2$, 740 mg/m$^2$, 750 mg/m$^2$, 760 mg/m$^2$, 770 mg/m$^2$, 780 mg/m$^2$, 790 mg/m$^2$, 800 mg/m$^2$, 810 mg/m$^2$, 820 mg/m$^2$, 830 mg/m$^2$, 840 mg/m$^2$, 850 mg/m$^2$, 860 mg/m$^2$, 870 mg/m$^2$, 880 mg/m$^2$, 890 mg/m$^2$, 900 mg/m$^2$, 910 mg/m$^2$, 920 mg/m$^2$, 930 mg/m$^2$, 940 mg/m$^2$, 950 mg/m$^2$, 960 mg/m$^2$, 970 mg/m$^2$, 980 mg/m$^2$, 990 mg/m$^2$, 1000 mg/m$^2$, or a number or a range between any two of these values, per dose or time period for a number of times or cycles.

In some embodiments, the effective amount of the agent co-administered with cerdulatinib (e.g., rituximab), whether for the dose of the first cycle and for the doses of the subsequent cycles, is, or is about, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg 1000 mg, or a number or a range between any two of these values, per dose or time period for a number of times or cycles.

In some embodiments, the time period between two consecutive doses is, or is about, every day, every two days, every three days, every four days, every five days, every six days, every week, every two weeks, every three weeks, every four weeks, every one month, every two months, every three months, every four months, every five months, every six months, every seven months, every eight months, every nine months, every ten months, every eleven months, every twelve months, or a number or a range between any two of these values. In some embodiments, the number of times or cycles is, is about, or is at most, 2, 3, 4, 5, 6, 7, 8, 9, 10, 11, 12, 13, 14, 15, 16, 17, 18, 19, 20, or a number or a range between any two of these values.

In some embodiments, the effective amount of the agent co-administered with cerdulatinib (e.g., rituximab) is co-administered with cerdulatinib in a concentration of about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL. 11 mg/mL, 12 mg/mL, 13 mg/mL, 14 mg/mL, 15 mg/mL, 16 mg/mL, 17 mg/mL, 18 mg/mL, 19 mg/mL, 20 mg/mL. 21 mg/mL, 22 mg/mL, 23 mg/mL, 24 mg/mL, 25 mg/mL, 26 mg/mL, 27 mg/mL, 28 mg/mL, 29 mg/mL, 30 mg/mL. or a number or a range between any two of these values.

In some embodiments, the agent co-administered with cerdulatinib (e.g., rituximab) is administered at least, or is administered at most, 5 times, 6 times, 7 times, 8 times, 9 times, 10 times, 20 times, 30 times, 40 times, 50 times, 60 times, 70 times, 80 times, 90 times, 100 times, or a number or a range between any two of these values.

4. Administration and Compositions

Cerdulatinib may be administered in pharmaceutical compositions comprising an effective amount of cerdulatinib and at least one pharmaceutically acceptable carrier or excipient.

Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

Suitable dosage forms, in part, depend upon the use or the route of administration, for example, oral, transdermal, transmucosal, inhalant, or by injection (parenteral). Such dosage forms should allow cerdulatinib to reach target cells. Other factors are well known in the art, and include considerations such as toxicity and dosage forms that retard the compound or composition from exerting its effects.

Cerdulatinib can be administered by different routes including intravenous, intraperitoneal, subcutaneous, intramuscular, oral, transmucosal, rectal, transdermal, or inhalant. In some embodiments, cerdulatinib can be administered by oral administration. For oral administration, for example, cerdulatinib can be formulated into conventional oral dosage forms such as capsules, tablets, and liquid preparations such as syrups, elixirs, and concentrated drops.

For inhalants, cerdulatinib may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. Cerdulatinib may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining cerdulatinib with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, cerdulatinib may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, cerdulatinib is formulated in sterile liquid solutions, such as in physiologically compatible buffers or solutions, such as saline solution, Hank's solution, or Ringer's solution. In addition, cerdulatinib may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions can be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In another embodiment, the carriers are those in which the active ingredient is soluble. Emulsifiers, stabilizers, humectants and antioxidants may also be included as well as agents imparting color or fragrance, if desired. Creams for topical application are formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art.

In some embodiments, cerdulatinib, or a pharmaceutically acceptable salt, co-crystal or solvate thereof, is administered orally without limitation with regard to food intake, for example, cerdulatinib can be administered with or without food.

EXAMPLES

Example 1

In a phase 1, dose-escalation study in adults with relapsed/refractory B cell malignancies, cerdulatinib was administered orally to sequential dose-escalation cohorts using once daily (QD) and twice daily (BID) schedules. Repeat CT scans were obtained from 6 patients with chronic lymphocytic leukemia (CLL) or small lymphocytic lymphoma (SLL), 13 patients with follicular lymphoma (FL), 12 patients with diffuse large B cell lymphoma (DLBCL), and 6 patients with mantle cell lymphoma (MCL). Correlation of tumor response with PD markers was determined in patients with CLL/SLL and FL, for whom meaningful clinical responses were observed.

Cerdulatinib was administered to sequential dose cohorts at increasing dose levels until the maximum tolerated dose (MTD) was identified. The starting dose level was 15 mg PO QD for 28 days (cycle 1), except on Days 2 and 3 of Cycle 1, when single-dose pharmacokinetic (PK) assessments were performed. If cerdulatinib was well tolerated, patients continued to receive treatment at the discretion of the investigator until discontinuation criteria were met.

Reagents for Pharmacodynamic Assays

For induction of cell signaling events, the following reagents were procured. Goat anti-human IgD (IgG fraction; Bethyl Laboratories Inc., Montgomery, Tex.), donkey anti-human IgM F(ab)'2 (Jackson ImmunoResearch, West Grove, Pa.), and recombinant human IL-2, IL-4, IL-6, and GM-CSF (R&D Systems, Minneapolis, Minn.). Lyse/Fix buffer and BD FACS/Lyse buffer (BD Biosciences, San Jose, Calif.) were used to prepare whole blood for intracellular and surface antibody staining, respectively. Cell lineages were identified by flow cytometry by using the antibodies: mouse anti-human CD3 APC-Cy7 and Alexafluor PE-CF594 conjugates, CD5 Alexafluor 700, CD14 APC, CD16 APC-Cy7, CD19 FITC and PerCP conjugates, CD20 PE-Cy7, and CD56 FITC (BD Biosciences). Intracellular phosphorylation events were detected using rabbit anti-human pSYK Y525/526 PE and pERK Y204 APC (Cell Signaling Technologies, Danvers, Mass.), and mouse anti-human pAKT 5473 PE-CF594, pSTAT3 Y705 PE, pSTAT5Y695 PE, and pSTAT6 Y641 PE conjugates (BD Biosciences). The CLL surface phenotype was monitored using cell lineage markers combined with mouse anti-human CD69 PE, CD86 PE-CF594, CD5 Alexafluor 700, and CXCR4 PerCP (BD Biosciences).

Bioanalysis, Pharmacokinetics and Pharmacodynamics

Blood samples were collected on K2EDTA for the determination of total cerdulatinib plasma concentrations on day 1 prior to dosing and at 0.5, 1, 2, 3, 4, 6, 8, and 12 hours post-dose; on Day 8 at pre-dose and 2 hours post-dose; on Day 15 pre-dose; and on Day 28 (end of the first treatment cycle) at pre-dose and at 0.5, 1, 2, 3, 4, 6, 8, and 12 hours post-dose. A liquid chromatography-tandem mass spectrometry (LC-MS/MS) method was developed and validated by Alturas Analytics, Inc. (Moscow, Id.) for the determination of cerdulatinib concentration in human plasma. Plasma PK analytical methods are described in Coffey, G., et al., *The novel kinase inhibitor PRT062070 (Cerdulatinib) demonstrates efficacy in models of autoimmunity and B-cell cancer*. J Pharmacol Exp Ther, 2014. 351(3): p. 538-48. Chromatographic separations were performed over a Phenomenex Synergi Polar-RP column (50×2.0 mm, 4 µm) (Phenomenex, Torrance, Calif., USA). MS/MS analysis was performed using a Sciex API-4000 triple quadrupole mass spectrometer with a TurboSpray ion source (Applied Biosystems, Foster City, Calif., USA). The peak area of the m/z 394→360 cerdulatinib product ion was measured against the peak area of the m/z 397→363 internal standard product ion. Intra-assay precision (% CV) and accuracy (% bias) were within 0.8% to 4.5% and −10.1% to 7.8%, respectively, and inter-assay precision (% CV) and accuracy (% bias) were 2.0% to 3.8% and −7.3% to 6.0%, respectively.

For PD assessments, serial blood samples were drawn into lithium-heparin vacutainer tubes on Day 1 prior to dosing and again at 0.5, 1, 2, and 4 hours post-dose; on Day 8 at pre-dose and 2 hours post-dose; and Day 28 prior to dosing. Multiple assays were performed using the Day 1 and Day 8 PD samples. SYK-mediated BCR signaling in whole blood was measured prior to and post-dosing by stimulating 100 µL whole blood with 2 µL of anti-human IgD (IgG fraction) and 10 µg anti-human IgM for 10 minutes at 37° C., measuring the induction of pSYK Y525/526, pAKT S473, and pERK Y204. Similarly, whole blood was stimulated with 10 ng/mL of IL-2 (JAK1/3-dependent), IL-4 (JAK1/3-dependent), IL-6 (JAK1/TYK2-dependent) or GM-CSF (JAK2-dependent) for 20 minutes, measuring the induction of pSTAT5 Y694 in T-cells and NK cells, the induction of pSTAT6 Y641 in B cells, T-cells, NK cells, and monocytes, the induction of pSTAT3 Y705 in monocytes, B cells, and T-cells, and the induction of pSTAT5 Y694 in monocytes, respectively. The technical details for these assays were described in Coffey, G., et al., J Pharmacol Exp Ther, 2014. 351(3): p. 538-48. With blood samples from the CLL patients only, tumor cell surface expression of CD5, CD69, CD86, and CXCR4 pre-dose on days 1 and 28 were monitored. The recommended volume of antibodies were applied directly to 100 µL whole blood and incubated for 1 hour at room temperature. Afterwards, 4 mL of BD Lyse/Fix reagent was added to the blood to lyse red blood cells and fix the remaining leukocytes, followed by washing and FACS analysis. For each assay, data were collected using an LSR II instrument (BD Bioscience, San Jose, Calif.) and analyzed using Flowjo software (Flowjo LLC, Ashland, Oreg.). Data were normalized to the induction of each parameter prior to dosing on day 1 to generate percent inhibition post-dosing.

Whole blood for isolation of serum was collected prior to dosing on days 1, 8, and 28 to measure changes in protein markers of inflammation and immune function. Serum samples were snap-frozen on dry ice immediately following its separation and stored at −80° C. Samples were analyzed using a multiplexed luminex-based technology (Myriad RBM, Austin, Tex.), utilizing the companies ImmunoMap (40 analytes) and InflammationMap (45 analytes) platforms. Serum from healthy donors was used as control.

Peripheral blood B cells were isolated at baseline from CLL patients using the RosetteSep B cell isolation kit, following the manufacturer's protocol (Stem Cell Technologies, Vancouver, Canada). Cells were washed twice in phosphate buffered saline and snap-frozen as a pellet on dry ice. Cell pellets, along with formalin-fixed, paraffin-embedded archival tumor sections, were delivered to the Department of Genomic and Molecular Pathology at the University of Chicago Medical Center, where DNA was isolated using standard methods and subjected to next generating sequencing (NGS) using Hi-Seq 2500, see Kadri, S., et al., *Clinical Validation of a Next-Generation Sequencing Genomic Oncology Panel via Cross Platform Benchmarking against Established Amplicon Sequencing Assays*. J Mol Diagn, 2017. 19(1): p. 43-56.

Statistical Analysis

The data were analyzed using the statistical language R and the accessory packages ggplot2 (Wickham, H., *Elegant Graphics for Data Analysis*. 2016: Springer-Verlag) and drc (Ritz, C., et al., *Dose-Response Analysis Using R*. PLoS One, 2015. 10(12): p. e0146021). For cell signaling assays, percent inhibition was determined by normalizing the receptor-induced phosphorylation events mean fluorescent intensity (MFI) to that of pre-dose receptor-induced MFI. The resulting relative activities were analyzed by nonlinear regression to a 3-parameter log-logistic function with an upper and lower limit set at 100 and 0%. For the analysis of immune and inflammation markers in serum, the varying concentration units were converted to a common scale in pg/mL. Values below and in excess of the detection limit were replaced by half the detection limit and the upper limit, respectively. For missing values, the median value for each marker from the treatment group was imputed. Statistically significant differences between the healthy and patient serum marker at all cycles (Cycle 1 Day 1, Cycle 1 Day 8, and Cycle 2 Day 1) were detected by paired t test. Dimension reduction of expression of the biomarker table in healthy and patient serum was performed using linear discriminant analysis, as is implemented in R. For the biomarkers and tumor response, reduction in biomarker after treatment was normalized to that before treatment and correlated to the maximal tumor response (growth or reduction), representing the ratio of minimal tumor area following treatment and tumor area before treatment. The significance of the relation between maximum tumor response and change in a specific biomarker was evaluated using Spearman-Rank-correlation and p value.

It was noted that steady state $C_{max}$ and AUC did not clearly affect tumor response, but preliminary analysis suggested that steady state $C_{min}$ ($SSC_{min}$) did. The dose-escalation study revealed that $SSC_{min}$ of up to 1 μM was well tolerated. The CLL/SLL patients for the most part were in lower dose cohorts, achieving $SSC_{min}$ of 0.004-0.325 μM (FIG. 1). At this exposure, 3 of 5 patients achieved >50% nodal reductions. The one CLL patient who achieved higher exposure came on study following an aggressive relapse on ibrutinib, and did not respond to cerdulatinib. The FL patients appeared to have a different response to cerdulatinib, and tumor responses were more apparent at $SSC_{min}$ exposures in the range of 0.729-1.219 μM (FIG. 1). At this higher exposure range, 3 of 6 patients achieved a partial response (including one which was a transformed FL patient, grade 3B), whereas lower $SSC_{min}$ resulted in 2 stable diseases and 1 progressive disease.

Relationship Between Tumor Response and SYK/JAK Inhibition

The potency and selectivity for target inhibition following oral dosing in patients using a variety of whole blood assays was measured. High level inhibition of BCR-induced SYK auto-phosphorylation (pSYK Y525/526) and downstream signaling to ERK (pERK Y204) and AKT (pAKT S473) was observed at tolerated exposures. Similarly, IL-2, IL-4, and IL-6 signaling (JAK1, JAK3, and TYK2 dependent) were potently inhibited in a concentration-dependent manner. To demonstrate specificity within the JAK family, we additionally performed GM-CSF stimulations on patient samples, which induce a JAK2-dependent STAT5 phosphorylation. Consistent with pre-clinical data, cerdulatinib demonstrated potent inhibition of SYK and JAK family members, sparing JAK2. No inhibition of PMA-mediated B cell pERK Y204 was observed, again demonstrating specificity of action.

Figure 2:
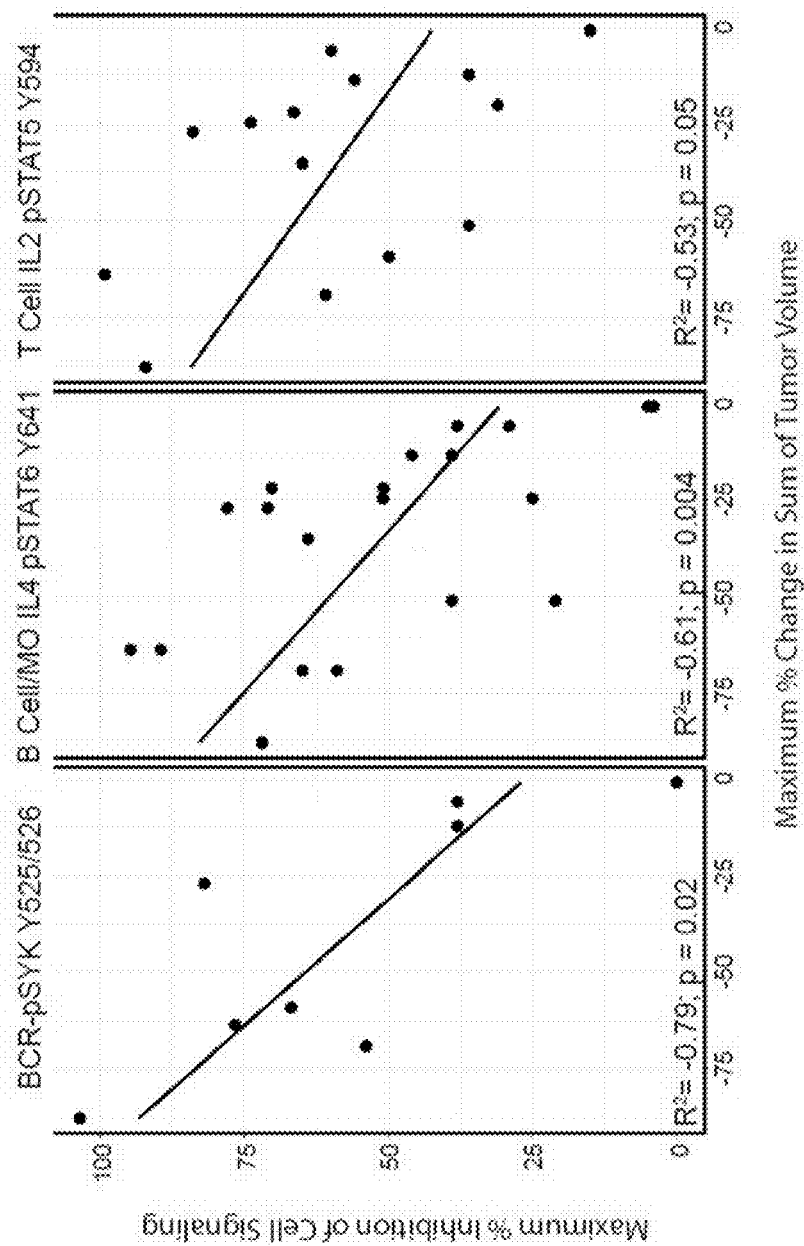
FIG. 2 shows tumor response as it relates to SYK/JAK inhibition.

The PK/PD relationships for all assays performed were evaluated to estimate $IC_{50}$'s. Measures of BCR-signaling were inhibited with $IC_{50}$'s in the 0.33-0.73 μM range. Depending on the cell lineage, measures of JAK/STAT signaling were inhibited with $IC_{50}$'s in the 0.19-1.11 μM range. The relationship between maximum % change in tumor volume and % inhibition of SYK and JAK signaling pathways in the whole blood assays is presented in FIG. 2. Inhibition of BCR-induced SYK auto-phosphorylation (pSYK Y525/526) significantly correlated with tumor response with an R of −0.79 (p=0.02). Four of the 5 patients in which pSYK Y525/526 was inhibited by >50% achieved a partial response. Inhibition of B cell and monocyte (data combined) IL-4 also significantly correlated with tumor response (R of −0.61; p=0.004), although several patients with high level IL-4 inhibition had marginal reductions in tumor size. This was also observed with inhibition of T-cell IL-2 signaling, which significantly correlated with tumor response (R of −0.53; p=0.05), despite the fact that several patients in which >50% inhibition of the pathway was achieved had marginal tumor responses. There was no relationship between inhibition of IL-6 signaling and tumor response.

Serum markers that were elevated at baseline but unaffected by cerdulatinib in both patient groups were HCC4, IL18, and MIG. Additionally, for CLL/SLL patients only, thrombospondin, BDNF, DKK1, MPO (myeloperoxidase), CD40, RANTES, MMP9, and ENA78 were significantly reduced at baseline when compared with healthy controls. Of these, MPO and CD40 serum levels were normalized with cerdulatinib treatment. For FL patients only, CD40 and BDNF were reduced at baseline relative to healthy, the latter being normalized with cerdulatinib treatment.

Limited inhibition of serum inflammation markers was observed in the aggressive lymphomas (DLBCL/MCL).

Figure 3:
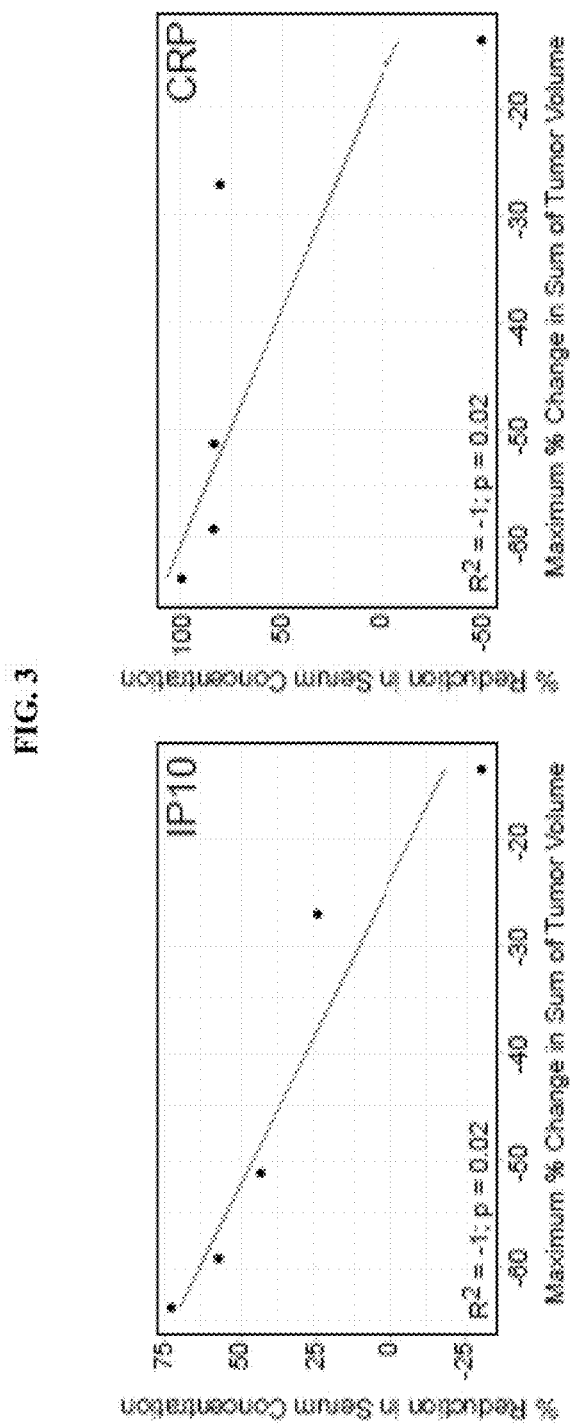
FIG. 3 shows inhibition of serum markers of inflammation significantly correlate with tumor response in CLL/SLL patients.
Figure 4:
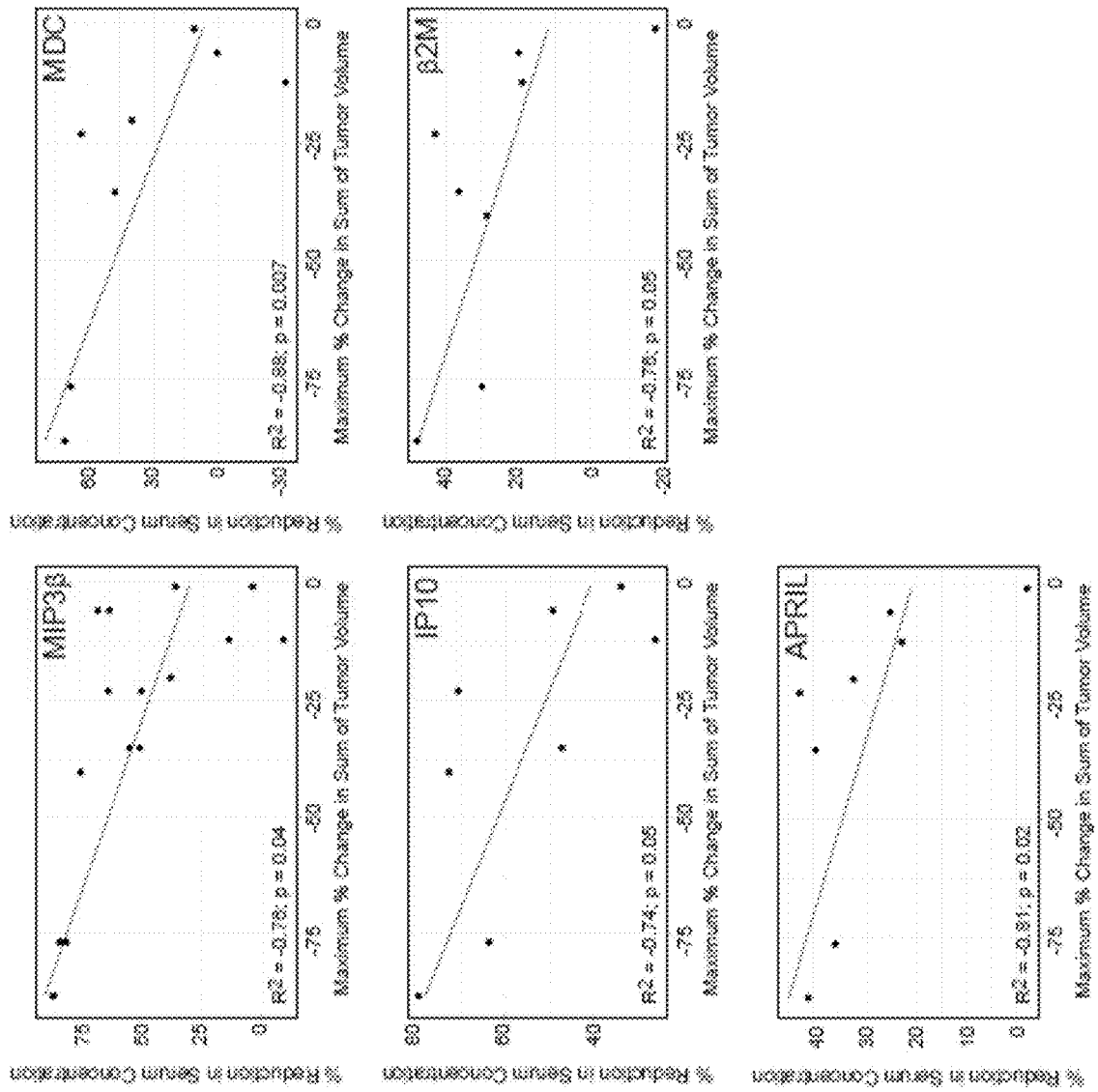
FIG. 4 shows inhibition of serum markers of inflammation significantly correlate with tumor response in FL patients.

Next, tumor response was related to % inhibition of serum markers of inflammation on Cycle 2 Day 1 (C2D1). Significant correlations between tumor response in CLL/SLL patients and reductions in serum CRP and IP10 were observed (FIG. 3). In FL patients, significant correlations existed between tumor response and inhibition of MIP3β, MDC, IP10, β2M, and APRIL (FIG. 4). Baseline serum concentrations of these proteins did not predict tumor response to treatment. These data demonstrate that cerdulatinib can modulate systemic inflammation, which for several proteins was associated with tumor response.

Relationship Between Markers of Inflammation and Tumor Response

Figure 5A:
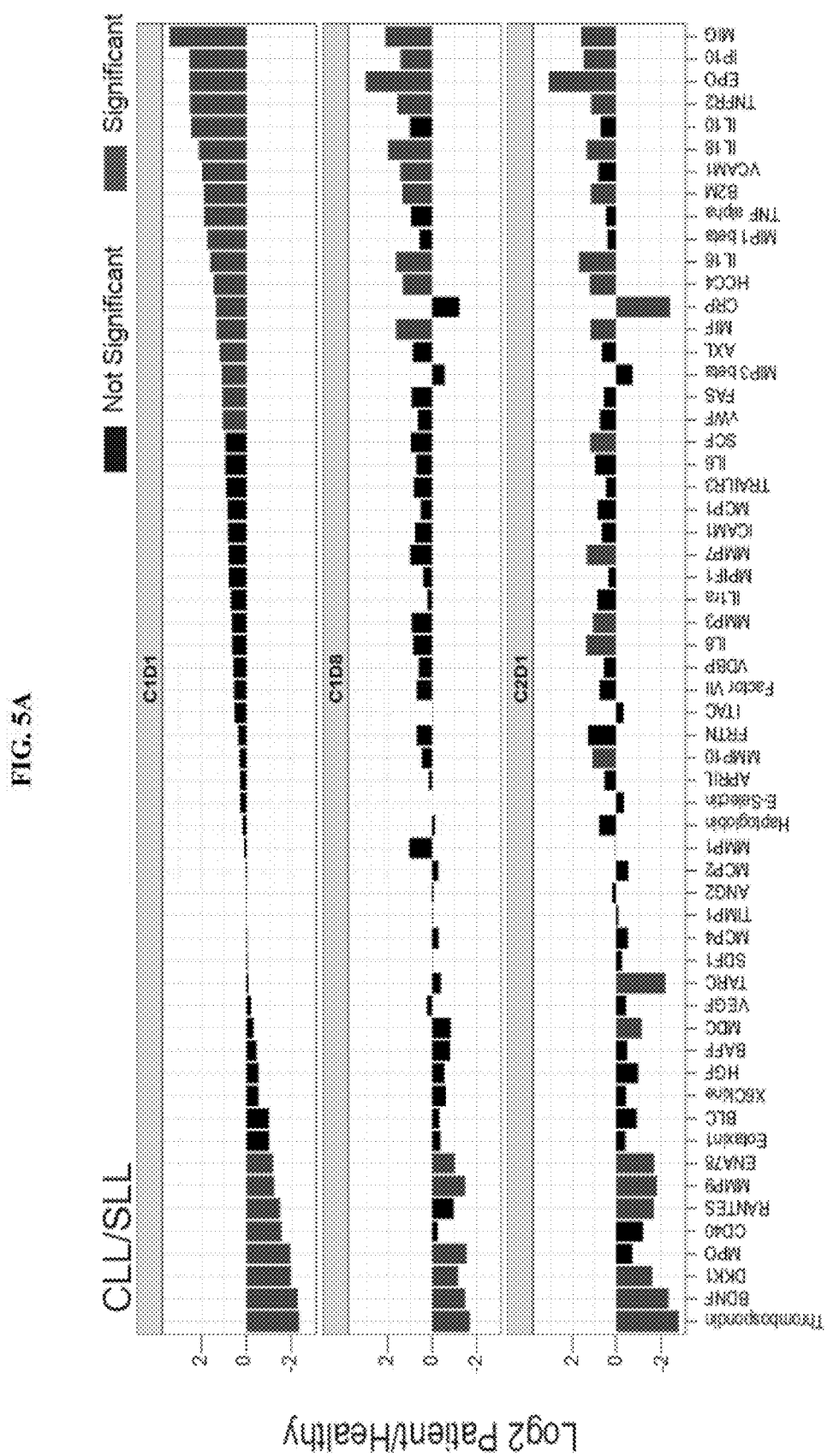
FIG. 5A shows significant inhibition of serum markers of inflammation in CLL/SLL patients following treatment with cerdulatinib.
Figure 5B:
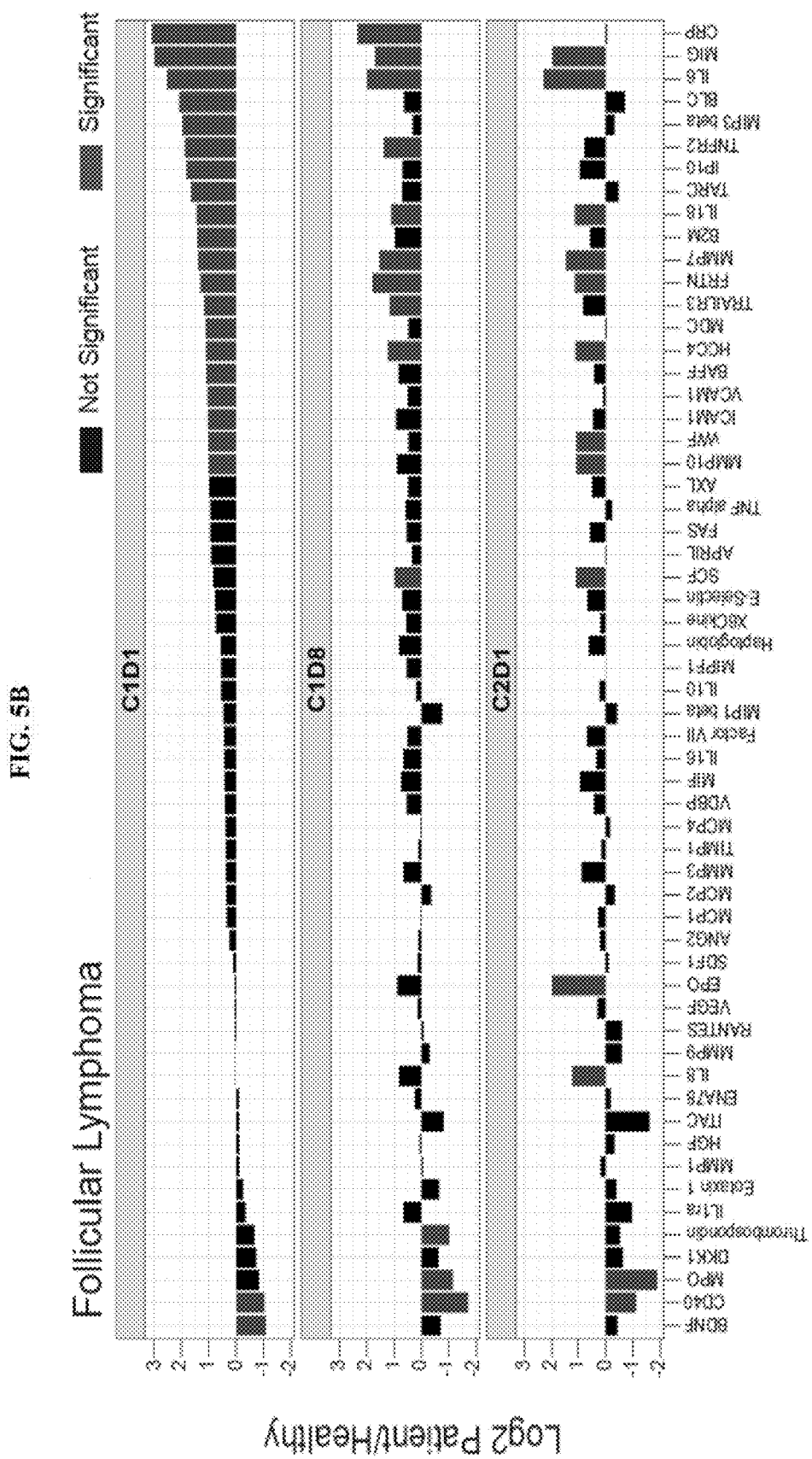
FIG. 5B shows significant inhibition of serum markers of inflammation in FL patients following treatment with cerdulatinib.

Cancer patients often present with underlying inflammation that can be detected by serum protein profiling. To evaluate this, and determine the effect of cerdulatinib on systemic inflammation, serial serum samples collected from patients were analyzed for serum proteins associated with inflammation and general immune function. Serum concentrations of 90 proteins were determined, of which 31 were consistently below limits of detection. FIG. 5A and FIG. 5B represent an analysis of the remaining 59 proteins for which measurements were possible. At baseline, the inflammatory profile of CLL/SLL and FL patients was quite divergent, and could be distinguished from each other and healthy controls by cluster analysis, lending confidence to the validity of the data.

In both CLL/SLL and FL patients, the common serum markers that were significantly elevated at baseline (Cycle 1 Day 1; C1D1) were vWF, MIP3β, CRP, HCC4, β2M, VCAM1, IL18, TNFR2, IP10, and MIG (FIG. 5A and FIG. 5B). By Cycle 1 Day 8 (C1D8) and Cycle 2 Day 1 (C2D1), several of these markers lost significance relative to healthy, indicating a normalization of inflammation with cerdulatinib treatment. For the most part, reductions in serum markers of inflammation occurred within the first 8 days of therapy with cerdulatinib, by Cycle 1 Day 8 (C1D8). Cerdulatinib significantly reduced MIP30, CRP, and VCAM1 in both CLL/SLL and FL patients.

Clinical Responses

Figure 6A:
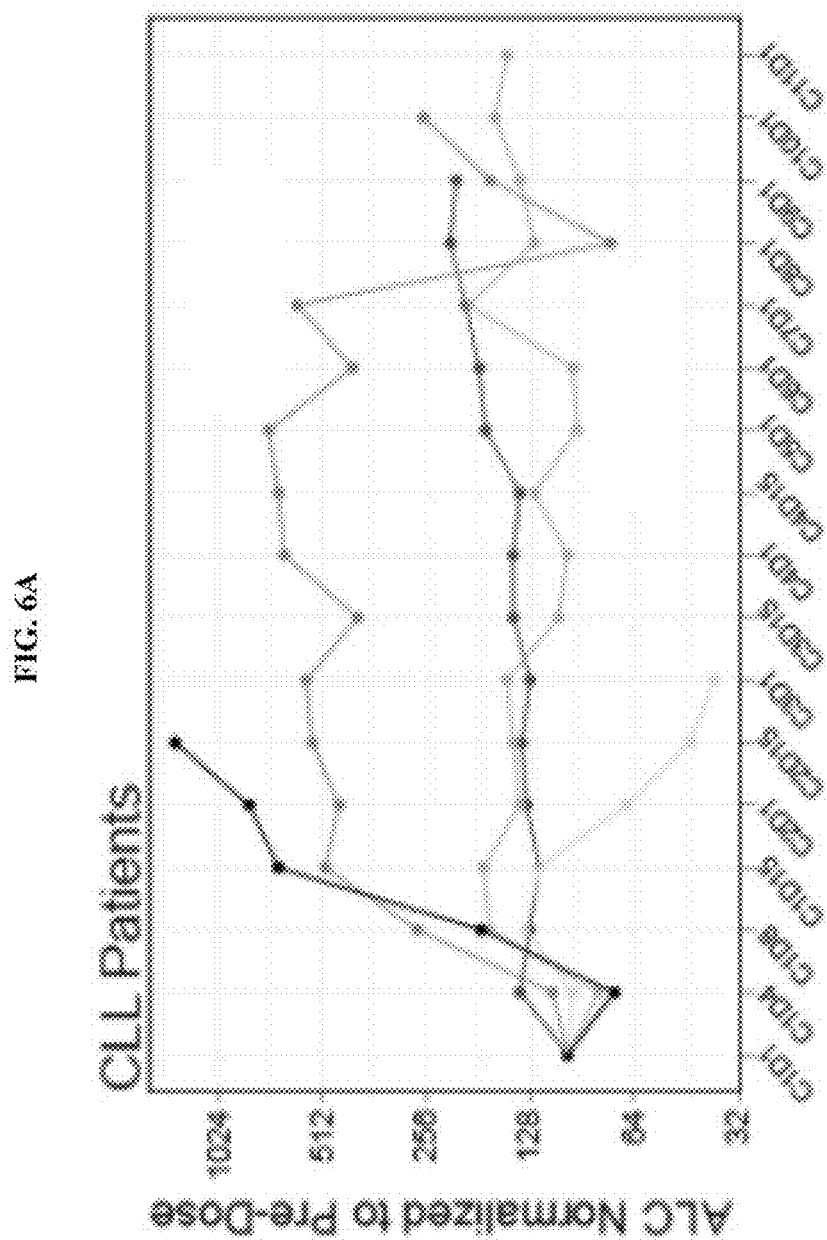
FIG. 6A and FIG. 6B show cerdulatinib treatment-related increases in blood absolute lymphocyte counts (ALC) occurred in CLL/SLL (FIG. 6A) and FL patients (FIG. 6B), respectively.
Figure 6B:
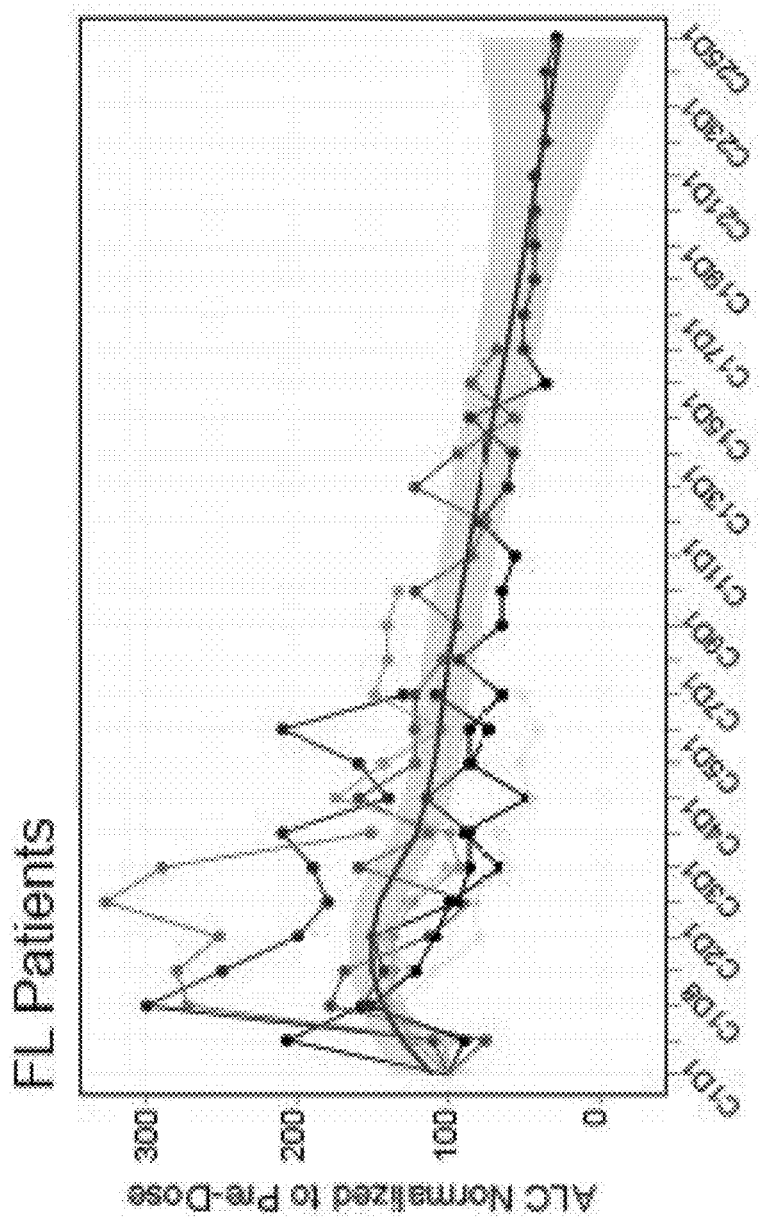
Figure 7A:
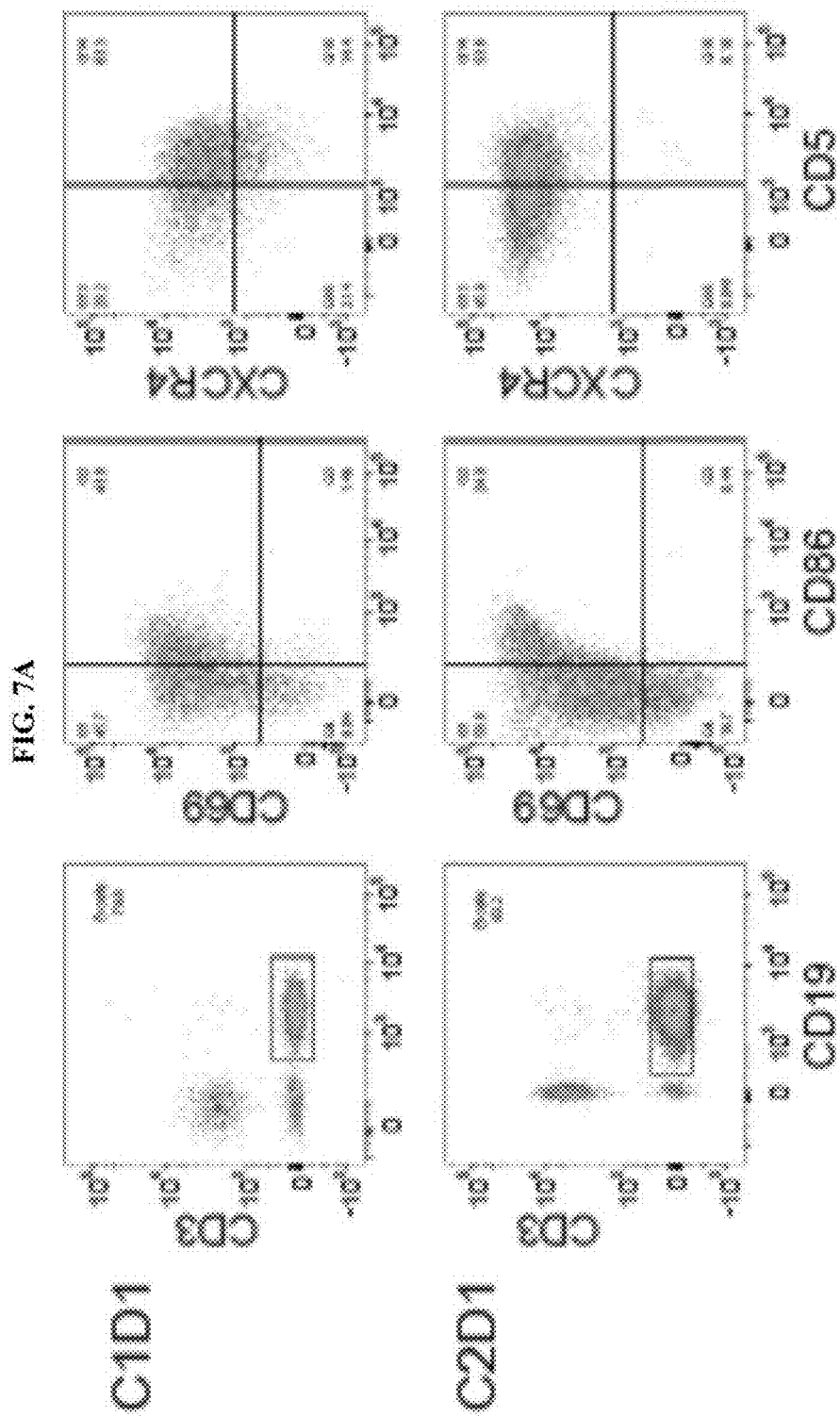
FIG. 7A and FIG. 7B show cerdulatinib treatment-related changes in tumor cell surface activation and homing markers in a CLL patient having 52% nodal reduction (FIG. 7A) and a CLL patient having 59% nodal reduction (FIG. 7B), respectively.
Figure 7B:
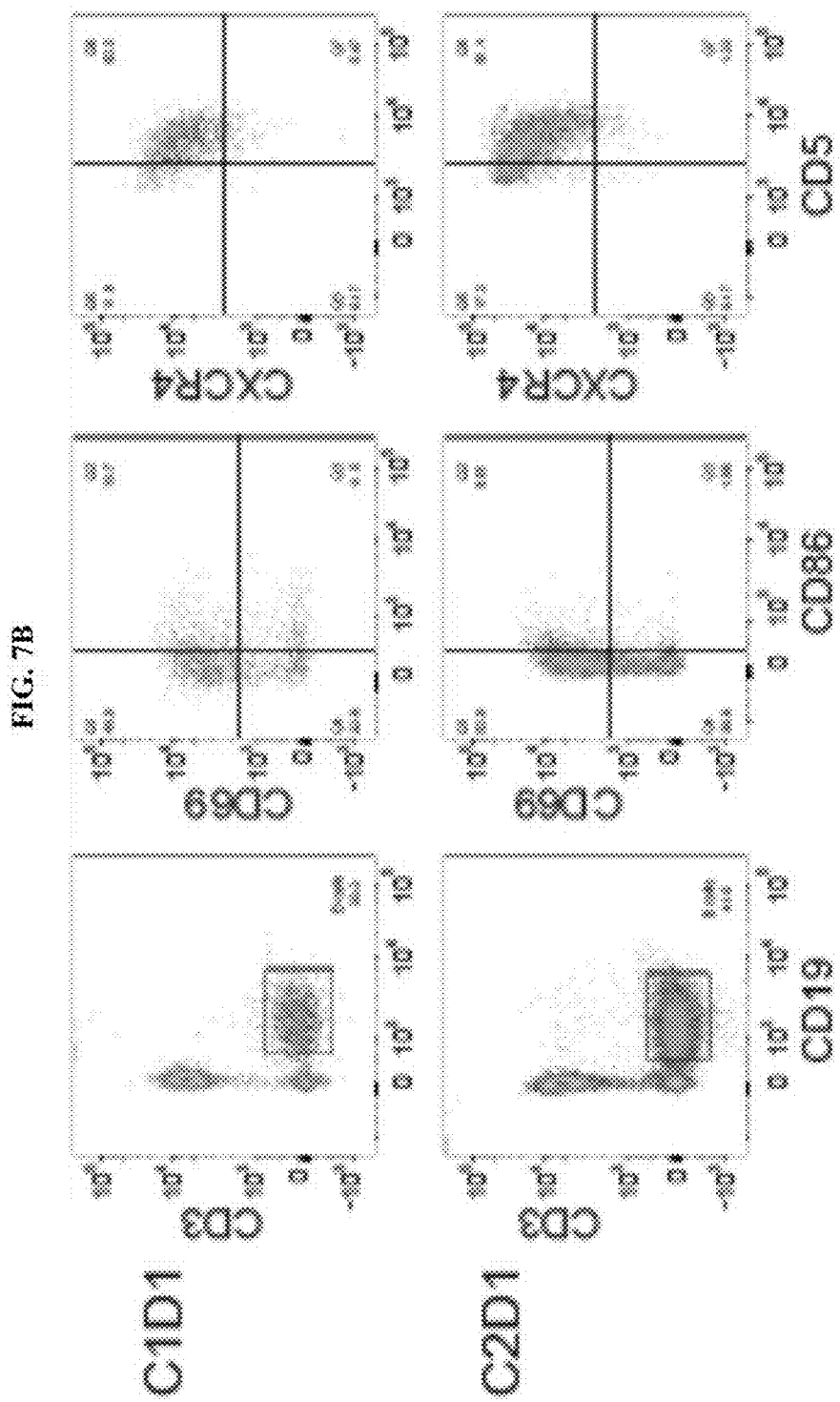

Treatment-related increases in blood absolute lymphocyte counts (ALC) occurred in both CLL/SLL and FL patients (FIG. 6A and FIG. 6B). Of the 6 CLL/SLL patients treated with cerdulatinib, 5 remained on drug long enough to monitor ALC, which were elevated 0.3-10 fold relative to pre-treatment. For two of these patients, treatment-related changes in tumor cell surface activation and homing markers were additionally evaluated (FIG. 7A and FIG. 7B). As shown in the ALC plots over time (FIG. 6A and FIG. 6B), by the beginning of the second cycle of treatment (Cycle 2 Day 1; C2D1) there was considerable mobilization of tumor cells into the peripheral blood. FACS analysis of these cells prior to treatment (Cycle 1 Day 1; C1D1) and again at Cycle 2 Day 1 (C2D1) revealed decreased expression of the surface activation markers CD69 and CD86, as well as reduced CD5 expression (a negative regulator of BCR signaling) and enhanced CXCR4 expression (responsible for cell homing to lymphoid tissues). These data suggest that cerdulatinib mobilizes tumor cells into the periphery and prevents their return to secondary lymphoid organs.

Genetic abnormalities were monitored by next generation DNA sequencing using OncoPlus, a panel of 1,212 cancer-related genes (Kadri, S., et al., *Clinical Validation of a Next-Generation Sequencing Genomic Oncology Panel via Cross-Platform Benchmarking against Established Amplicon Sequencing Assays*. J Mol Diagn, 2017. 19(1): p. 43-56). Fresh tumor samples were obtained from the peripheral blood of 6 CLL patients prior to dosing with cerdulatinib, as well as archival tumor biopsies obtained from 4 FL patients and 1 MCL patient. A list of the mutations observed is detailed in Table 3.

increased MYC, BCL2, and BCL6 expression by immunohistochemistry ("triple-hit" lymphoma).

Figure 8:
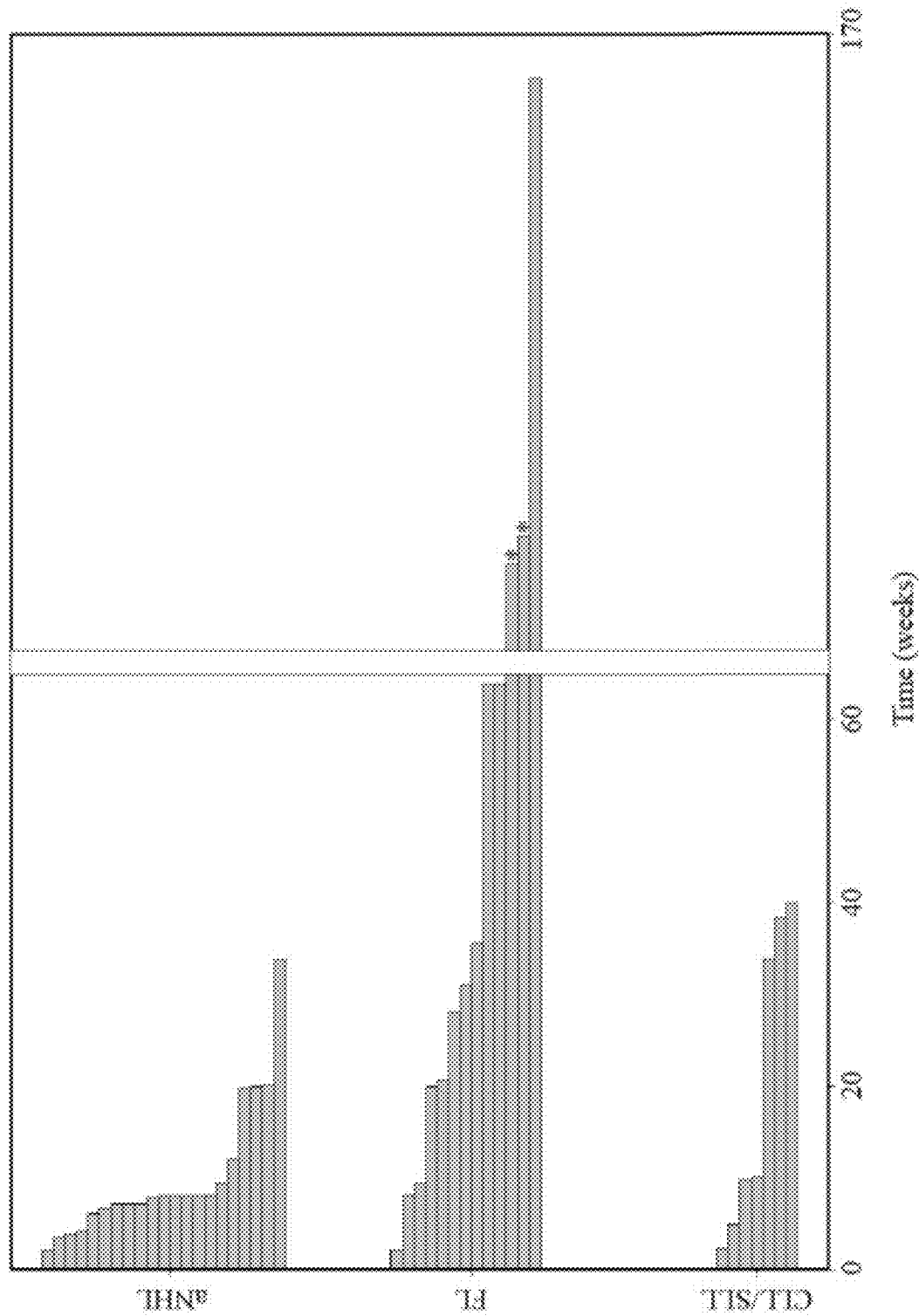
FIG. 8 shows the duration of time on cerdulatinib for each of the dosed patients in Example 1.

Patients with FL had the greatest median duration of exposure, 33.9 weeks relative to CLL/SLL and aNHL with 11.2 and 7.9 weeks, respectively. The duration of time on cerdulatinib for each of the dosed patients is shown in FIG. 8.

Phosphorylation events more distal to the BCR, namely pERK Y204 and pAKT S473, appeared to be more potently inhibited relative to the SYK Y525/526 auto-phosphorylation site, possibly reflecting a threshold for SYK inhibition at which the signaling pathway is shut off. It was estimated that the $IC_{50}$ of cerdulatinib against BCR signaling to be in the range of 0.17 to 0.74 µM following oral dosing, reflecting the lower and upper limit confidence intervals for ERK and AKT. The two assays performed that monitored JAK/STAT pathway activation in B cells were IL-4 and IL-6 induced pSTAT6 Y641 and pSTAT3 Y705, respectively. Inhibition of IL-4 signaling was quite variable among patients, with an average $IC_{50}$ of 1.08 µM (CI; 0.36-1.79 µM). IL-6 signaling was inhibited with more consistent potency across patients with an average $IC_{50}$ of 0.22 µM (CI; 0.14-0.61). Importantly, inhibition of BCR-mediated SYK Y525/526 and IL-4-mediated pSTAT6 Y641 both significantly correlated with tumor response. These correlations lend support to the proposed mechanism of cerdulatinib anti-tumor activity.

During the dose escalation study, a complete inhibition of most SYK and JAK signaling assays was achievable at tolerated exposures. The selected phase 2 dose of 30 mg twice daily targets a $SSC_{min}$ of approximately 0.8 µM, which is expected to maintain >50% inhibition of SYK and JAK in

TABLE 3

| Patient | Disease | % Change in Tumor (CT) | Relevant Mutations |
|---|---|---|---|
| 1 | Ibrutinib relapsed CLL | 100 | EP300, P53, $BTK^{C481}$, NOTCH1, SPEN, PIK3R1, PCDHGA2, MYOM2, KMT2D |
| 2 | Ibrutinib relapsed CLL | 100 | EP300, TP53, $BTK^{C481}$, XPO1, WHSC1, MED12 |
| 3 | MCL | 42 | ID3, SETD2, WHSC1, KMT2C, ATM, KMT2D, SOCS1, MED12 |
| 4 | FL | 1 | NOTCH2, FAT3, FAT4, EGR2, CREBBP, KLHL14, ASXL1 |
| 5 | FL | −6 | FAT4, CCND3, MYOM2, KMT2D, BCL2, ZMYM3 |
| 6 | FL | −12 | BCL6, FAT4, NOTCH1, KMT2D, BCL2, TCF3 |
| 7 | CLL | −14 | NOTCH1, TP53, SETD2, SIGLEC10 |
| 8 | FL | −20 | ARID1A, $STAT6^{S864}$, AXIN1, CD79B, ZMYM3 |
| 9 | CLL | −27 | SPEN, PCLO |
| 10 | CLL | −52 | TET2, A20, MK167, FAT3, ATM, KRAS |
| 11 | CLL | −59 | NOTCH1, REL, HIST1H1E, KMT2C |
| 12 | CLL | −64 | KMT2D, MK167, TP53, SF3B1 |

Clinical activity was observed in CLL patients bearing mutations to NOTCH1, ATM, TP53, and KRAS. One of the responding patients bore a 17p deletion encompassing the TP53 locus. Importantly, two patients with ibrutinib-relapsed CLL who progressed within the first cycle of therapy with cerdulatinib uniquely shared 3 mutations in common: TP53, EP300, and $BTK^{C481S}$. Genetic correlates in FL were more limited, with data on 4 patients, 3 of whom had stable disease as best response to therapy and one progressed. Although the exposures are well below that obtained by the phase 2 dose (30 mg BID, $SSC_{min}$~0.8 µM), the two best responding patients with whom there was genetic information bore mutations to ZMYM3, KMT2D, FAT4, BCL2, BCL6, and STAT6. Lastly, strong clinical activity was observed in a transformed FL patient who presented with most whole blood assays throughout the day. The exposure peak-to-trough as measured in peripheral blood is roughly 2:1 in patients, indicating that the phase 2 dose will achieve near-complete inhibition of SYK/JAK signaling networks throughout the day. Exposure and extent of target inhibition in the actual tumor microenvironment is unknown, however, and may therefore be higher or lower than what we estimate from the whole blood assays.

The patients enrolled in this trial presented with varying degrees of inflammation. The nature of the inflammatory response was divergent enough among the disease subgroups and healthy normal subjects such that clustering analysis could distinguish them. If it is assumed that a failed immune response to the tumor has resulted in an inflammatory environment that now supports tumor growth and survival, then suppressing these inflammatory signals could negatively impact the tumor. Cerdulatinib rapidly (within first week of therapy) and significantly reduced the serum concentrations of several protein markers of inflammation. Moreover, reductions of several of these serum proteins with time on therapy significantly correlated with tumor response. In FL, these were APRIL, β2M, IP10, MDC, and MIP3β. These data suggest that one mechanism by which cerdulatinib may exert anti-tumor activity is by disruption of key signals responsible for the organization of the tumor microenvironment.

DNA was prepared from formalin-fixed archival tumor sections from 4 patients with FL and one with MCL, in addition to pre-treatment isolation of circulating CLL tumors from whole blood and subjected to next generation sequencing. This limited data set offered hints into a pharmacogenomics relationship. The two CLL patients who did not respond to cerdulatinib had relapsed on ibrutinib prior to study entry and presented with an aggressive disease. Both of these patients carried missense mutations to EP300 (Ser697Arg in one and Cys1247Phe in the other), TP53 (Glu285Lys in one and Arg273Cys in the other), and BTK (Cys481Ser in both). Interestingly, one patient with FL who relapsed following 5 prior therapies including progressive disease on bendamustin/rituximab, progressive disease on ibrutinib, and a less than 4 month response to R-CHOP as their last three therapies, contained a novel mutation to STAT6 (Ser86Ala), which is contained within the STAT dimerization domain. This patient achieved $SSC_{min}$ to $SSC_{max}$ cerdulatinib serum concentrations of 0.32-0.38 µM, which is considerably lower than our phase II exposure, and yet demonstrated a 20% reduction in tumor bulk with >6 month durability of response. Additional mutations associated with the three CLL patients with greatest nodal reductions were REL (Ile354Thr), a component of NFkB2, TET2 (Met66Leu), a dioxygenase that regulates DNA methylation status, A20 (Gln150Arg), an inhibitor of NFkB, and HIST1H1E (Ala47Val).

In summary, data from the phase 1 dose-escalation study identified a phase 2 dose that was well tolerated, achieved drug levels which resulted in high level inhibition of SYK and JAK signaling pathways and demonstrated evidence of anti-tumor activity. The phase 2 study is ongoing to establish safety and efficacy of cerdulatinib in CLL/SLL and FL patients.

Example 2

This study intended to confirm the safety and efficacy of cerdulatinib dosed 30 mg orally BID in patients with relapsed/refractory (r/r) B- and T-cell lymphoma. Dose reductions were permitted to a minimum of 15 mg BID. Response was assessed by Lugano Classification criteria.

Ninety nine patients enrolled (FL: 36, CLL/SLL: 28, PTCL: 18, marginal zone lymphoma: 8, aggressive: 5, Waldenstrom's macroglobulinemia: 4) (Table 4). Median age is 68 (42-93) and median # of prior therapies is 3 (1-13) (Table 5). 30 patients had prior BTK, PI3K or BCL-2 inhibitor therapy. The most common AEs of any grade are diarrhea (42%), fatigue (36%), and nausea (32%). Grade 3+ AEs occurring in ≥5% patients are neutropenia (18%), lipase increase (15%), pneumonia (12%), diarrhea (10%), and fatigue (7%). 5 patients have had Grade 5 infections considered related to study drug (3 of 5 in the CLL cohort). The target PK range has been achieved with an average $SSC_{min}$ of ~0.8 µM.

61% ORR in CLL/SLL, 49% in FL, and 47% in PTCL (5 CRs, 2 PRs in 15 patients) were seen (Table 6). The first PTCL patient achieved a CR and is on drug at 11 months. Responses typically occurred after 2 cycles of treatment. Durable PRs have occurred in patients who relapsed on BTK inhibitor (CLL, 5+ months, WM, 7+ months, FL, 12 months), venetoclax (SLL, 18+ months), and tenalisib (PTCL, 3+ months) therapy. Updated PK/PD, safety and efficacy will be presented.

Eighteen of the patients are relapsed/refractory PTCL patients, which included PTCL-NOS (7), AITL (6), ALCL (2), HSTCL (1), Gamma-delta TCL (1), and EITL (1); median age 70 [48-84]; prior transplant 28%; and 44% refractory to last therapy. Eleven patients were evaluated for clinical response, 3 discontinued prior to evaluation (2 due to progression; 1 withdrew consent), and 4 patients have yet to be evaluated. Seven patients have responded (ORR 47%). Of these, 5 achieved a CR after 2 cycles, 2 achieved a PR, and 2 SD. The majority of responses were observed in PTCL-NOS and AITL.

Although the durability of the cerdulatinib response in PTCL is still pending, the first two patients achieving a response (both CRs) are still on drug with response durations of 10 and 6 months, respectively (which corresponds to 12 and 8 months on treatment, respectively). A patient with CR was referred to allogeneic transplant and censored after cycle 2. An additional patient achieved complete remission of target lesions, but discontinued therapy due to a new lesion.

Importantly, CRs and PRs occurred in patients who failed multiple lines of therapy, including CHOP, brentuximab+rituximab, rituximab+CHOP, gemcitabine+oxiplatin, gemcitabine, high-dose steroids, lenalidomide, EPOCH, BEAM, BEAM/R-CHEP, ABVD, ixazomib, bosutinib, fenretinide, pralatrexate, romidepsin, belinostat, and an investigational PI3K inhibitor, RP-6530. One AITL patient who achieved CR with cerdulatinib had 10 different prior treatments and experienced PD under romidepsin, bosutinib, brentuximab, and gemcitabine+oxiplatin treatments.

The most common AEs of any grade were diarrhea (33%), fatigue (22%), lipase increase (17%), and nausea (17%). Grade 3+ AEs occurring in ≥2 patients are neutropenia (4), diarrhea (3), lipase increase (2), and pneumonia (2). The target PK range was achieved with an average $SSC_{min}$ of ~0.8 µM.

TABLE 4

| Initial dose | CLL/SLL | FL | Other iNHL* | PTCL | aNHL** | Total |
| --- | --- | --- | --- | --- | --- | --- |
| 35 mg BID | 6 | 2 | 4 | 0 | 5 | 17 |
| 30 mg BID | 22 | 34 | 8 | 18 | 0 | 72 |
| Total | 28 | 36 | 12 | 18 | 5 | 99 |

*indolent lymphoma
**aggressive lymphoma

TABLE 5

|  | CLL/SLL n = 28 | FL n = 36 | Other iNHL n = 12 | PTCL n = 18 | aNHL n = 5 | All N = 99 |
|---|---|---|---|---|---|---|
| Male sex, n (%) | 16 (57) | 19 (68) | 8 (67) | 8 (73) | 4 (80) | 55 (65) |
| Median age, years [range] | 70 [52-93] | 64 [42-88] | 65 [45-88] | 70 [48-84] | 78 [61-93] | 68 [42-93] |
| Median # of prior regimens [range] | 3 [1-13] | 3 [1-8] | 3 [1-5] | 3 [1-9] | 3 [1-4] | 3 [1-13] |
| Prior Therapies, n (%) | | | | | | |
| Anti-CD20 antibody | 27 (96) | 35 (97) | 12 (100) | 3 (17) | 5 (100) | 82 (83) |
| Bendamustine | 10 (36) | 19 (53) | 5 (42) | 2 (11) | 1 (20) | 37 (37) |
| Any alkylating agent | 21 (75) | 31 (86) | 10 (83) | 16 (89) | 5 (100) | 83 (84) |
| Fludarabine | 9 (32) | 0 | 0 | 0 | 0 | 9 (9) |
| Anthracyclines | 5 (18) | 17 (47) | 3 (25) | 14 (78) | 3 (60) | 42 (42) |
| Any BCR pathway inhibitor | 13 (46) | 10 (28) | 3 (25) | 2 (11) | 1 (20) | 29 (29) |
| Refractory disease, n (%) | 11 (39) | 11 (39) | 6 (50) | 8 (44) | 0 | 36 (36) |

TABLE 6

| Response | CLL/SLL | FL | Other Indolent Lymphoma | DLBCL, tFL, and MCL | PTCL |
|---|---|---|---|---|---|
| N: | 28 | 31 | 12 | 5 | 15 |
| ORR | 61% | 49% | 42% | 20% | 47% |
| CR (%) | 1 (4) | 3 (10) | 0 | 0 | 5 (33) |
| PR (%) | 16 (57) | 12 (39) | 5 (42) | 1 (20) | 2 (13) |
| SD (%) | 2 (7) | 8 (26) | 2 (17) | 1 (20) | 2 (13) |
| PD (%) | 1 (4) | 3 (10) | 4 (33) | 3 (60) | 5 (33) |
| NE/Safety | 8 | 5 | 1 | 0 | 1 |

TABLE 7

Prior Therapies for PTCL Patients With a CR

| Disease | Prior therapies |
|---|---|
| PTCL-NOS | CHOP, Bendamustine-Rituximab, Bendamustine, Romidepsin |
| AITL | CHOEP → BEAM/ASCR |
| PTCL-NOS | EPOCH, Pralatrexate |
| AITL | BEAM |
| AITL | ABVD, Romidepsin, Romidepsin, Belinostat, RP-6530, Fenretinide |
| AITL | ABVD, CHOP, Romidepsin, Ixazomib, Bosutinib, Brentuximab, Gemcitabine-Oxaliplatin, HD-Steroids, Lenalidomide, RP-6530 |
| AITL | R-CHOP, Gemcitabine |

Both complete responses in PTCL-NOS have follicular involvement.

Cerdulatinib dose of 30 mg BID demonstrates good tolerability and efficacy in heavily pre-treated r/r B and T-cell NHL, including PTCL.

Example 3

CellTiter Glo, Edu and caspase 3 assays were used to examine the effects of cerdulatinib alone and in combination with venetoclax. Percent inhibition was determined relative to vehicle control. Edu incorporation and caspase 3 cleavage were performed using FACS-based assays and CellTiter Glo in a 96-well black plate.

Follicular lymphoma (FL) cell lines SU-DHL6, DOHH2, or WSU-FSCCL were treated with cerdulatinib in the presence or absence of venetoclax at the indicated concentrations for 24-72 hours and analyzed by Edu, CellTiter-Glo, Annexin V/PI, and CellTiter-Glo).

Whole cell lysates were subjected to immunoblotting on 12% gels and probed with the indicated antibodies using established protocols. Phosphoflow cytometry was performed on an LSRII following cell fixing in 4% PFA and permeabilzation with 50% methanol. Phospho-antibody staining was performed for 1 hour at room temperature.

Cerdulatinib was functional in FL cells lines and could inhibit basal expression of phospho (p)AKT and pERK as well as anti-IgM and anti-IgG mediated signaling.

Cerdulatinib synergized with venetoclax to induce apoptosis in CLL cells in part by down-regulation of MCL-1. This is important given upregulation of MCL-1 is a key resistance mechanism to venetoclax.

Irrespective of the assay used, the combination of cerdulatinib and venetoclax invariably led to more potent growth arrest and apoptosis in these FL lines.

Cerdulatinib had minimal impact on Bcl-2 expression in FL lines, but resulted in down modulation of Mcl-1, which was most pronounced in WSU-FSCCL cells, with minimal effect in the other lines. Bim increased at the RNA level in both WSU and DHL6 cells, whereas Mcl-1 RNA levels remained unchanged with cerdulatinib alone and in combination with venetoclax.

Xenograft studies in Nude mice were performed to evaluate cerdulatinib and venetoclax in combination. Nude mice were inoculated with 106 SU-DHL6 cells subcutaneously. Once tumors reached 200 mm$^3$, the mice were randomized into 4 groups: vehicle, cerdulatinib alone, venetoclax alone, or a combination of cerdulatinib and venetoclax. Cerdulatinib in combination with venetoclax resulted in a superior reduction in tumor growth compared to the other treatments.

In those tumors treated with cerdulatinib an increase in Bim expression was observed with no change in MCL-1, consistent with our in vitro data.

Example 4

Primary CLL cases were treated with and without IL-4/CD40 in the presence or absence of ibrutinib, idelalisib, entospletinib, PRT062607 or cerdulatinib (all 1 μM). Combination studies were performed with 10 or 100 nM venetoclax or 300 and 1000 nM S63846. Cell viability was assessed by annexin V/PI using flow cytometry and changes in protein expression by immunoblotting.

CLL cells were treated with IL-4/CD40L or the vehicle control and immunoblotting performed for Bcl-2 family protein expression. Basal Mcl-1, Bcl-XL and Bim protein was expressed at relatively low levels compared to Bcl-2. However treatment with IL-4/CD40L induced a substantial and significant increase in Mcl-1 and Bcl-XL compared to the vehicle control, whilst Bcl-2 and Bim expression remained relatively stable. CLL cells pretreated with ibrutinib, idelalisib, entospletinib, PRT062607 or cerdulatinib significantly reduced IL-4/CD40L induced Mcl-1 and Bcl-XL expression, however in all cases cerdulatinib produced a more robust inhibition of these proteins compared to the other kinase inhibitors. Interestingly treatment with all BCR kinase inhibitors resulted in an increase in Bim expression at both the RNA and protein levels. However at equivalent drug concentrations Bim was induced to greater levels following cerdulatinib treatment compared to idelalisib and ibrutinib. Bim co-localization with Bcl-2 and Mcl-1 proteins was investigated using immunoprecipitation. Bim co-localized largely with Bcl-2 and a lesser extent with Mcl-1 in all the CLL cases in vitro. Venetoclax and S63845 synergized with all BCR kinase inhibitors including cerdulatinib to induce greater levels of CLL cell death by displacing Bim.

Example 5

In an open-label, randomized, 3-period crossover study, healthy subjects received 30 mg cerdulatinib orally. The 3-period treatments were fasted, high-fat diet, and proton pump inhibitor (PPI) esomaprazole, with 14-day washout between treatments. Blood samples were collected up to 72 hours after cerdulatinib treatment. PK endpoints were area under the curve (AUC), maximum concentration ($C_{max}$), Time to $C_{max}$ ($T_{max}$), and half-live ($T_{1/2}$).

There were 22, 24, and 21 subjects in fasted, fed, and PPI groups, respectively. Compared to fasted group, food and PPI had no significant effect on AUC and $C_{max}$ of cerdulatinib, and $T_{1/2}$ was similar (Table 8). There was a small delay in median $T_{max}$ after cerdulatinib was taken with food.

Although there was a small increase in cerdulatinib exposure with food or PPI, there was no clinically relevant impact on PK of cerdulatinib. These preliminary results suggest that cerdulatinib could be administered regardless of food or PPI.

TABLE 8

Preliminary Cerdulatinib PK Parameters

| Treatment | | $T_{max}$ Median (h) | $T_{1/2}$ Mean (h) | $C_{max}$ Mean (ng/mL) | $AUC_{0-inf}$ Mean (hr*ng/mL) |
|---|---|---|---|---|---|
| Fasted | Geometric Mean | 4.0 | 14.5 | 168 | 3460 |
|  | % CV | (3.0-6.0) | 15.2 | 36.5 | 38.2 |
| Fed | Geometric Mean | 6.00 | 13.6 | 187 | 4060 |
|  | % CV | (4.0-12.0) | 18.4 | 26.0 | 36.1 |
| PPI | Geometric Mean | 4.0 | 14.5 | 170 | 3680 |
|  | % CV | (3.0-6.0) | 16.9 | 37.4 | 36.8 |
| Ratio Fed/Fasted (90% CI) |  |  |  | 1.11 (1.01-1.22) | 1.16 (1.10-1.22) |
| Ratio PPI/Fasted (90% CI) |  |  |  | 1.02 (0.92-1.12) | 1.06 (1.01-1.12) |

Example 6

Figures 9A, 9B:
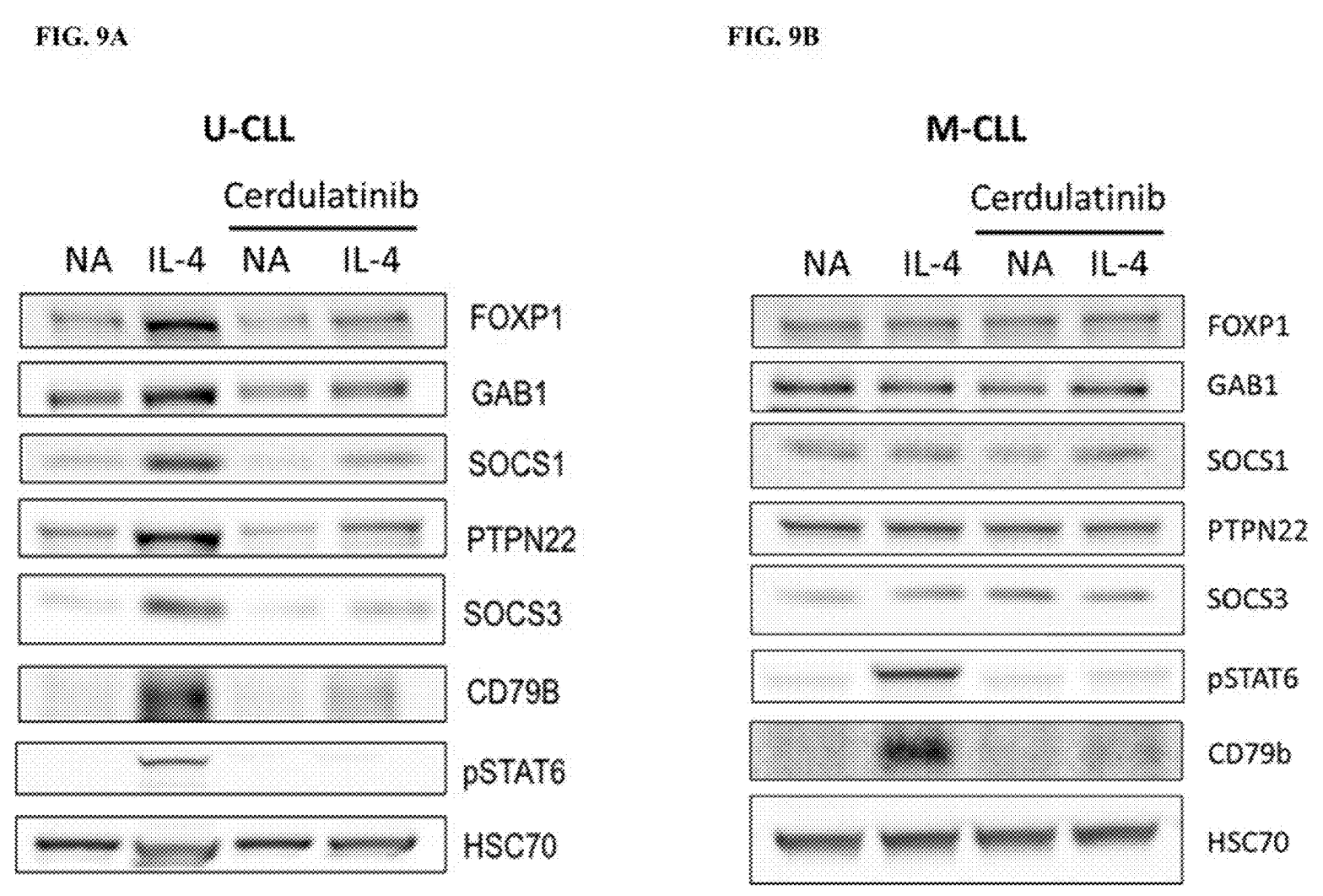

U-CLL cells and M-CLL cells were treated with and without 10 ng/mL IL-4 for 24 hours in the presence or absence of 1 μM cerdulatinib. Immunoblotting was used to protein expression among the different treatments. FIGS. 9A and 9B shows that IL-4 significantly increases the protein expression of GABA1, FOXP1, SOCS1, and SOCS3 while treatment with cerdulatinib suppresses this effect. FIGS. 10A-10G, 11A-11G and 12A-12G show the fold changes of the protein expression.

Example 7

The Dual SYK/JAK Inhibitor Cerdulatinib Demonstrates Rapid and Durable Tumor Responses in a Phase 2 Study in Patients with Relapsed/Refractory Follicular Lymphoma—as a Single Agent and in Combination with Rituximab Background:

Follicular B cell lymphoma (FL) is the most common indolent lymphoma, currently managed in the front-line setting with anti-CD20 monoclonal antibodies as a single agent or in combination with chemotherapy (i.e. CHOP, bendamustine). Based on current understanding of disease pathology, several targeted agents are under investigation in the relapsed/refractory (r/r) setting, underscored by the recent approvals of idelalisib, copanlisib duvelisib, targeting B cell antigen receptor signaling via inhibition of PI3K. Despite recent advances, there remains a need for well-tolerated and efficacious therapeutic options for r/r FL patients.

SYK is a key regulator of BCR signaling (upstream of BTK and PI3K), and its inhibition using entospletinib has demonstrated clinical activity in B cell malignancies (Sharman et al, 2013 and 2014; Walker et al, 2016). Importantly, FL growth may additionally be supported by autocrine or micro-environmental derived cytokines. Study of the FL tumor microenvironment suggests an important IL-4 signaling axis critical for survival. Compared with unaffected nodes, lymph nodes from patients with FL have greater numbers of follicular helper T cells that express high levels of IL-4 which appears to support the tumor via JAK1/3 pathway activation (Pangault et al, 2010).

Cerdulatinib is an oral, reversible ATP-competitive dual inhibitor of SYK and JAK family kinases (JAK1, JAK3, and TYK2) for the treatment of r/r FL, and previously reported a ~45% ORR in r/r FL when used as a single agent. Pre-clinical data also suggest synergy with venetoclax, presumably a consequence of cerdulatinib-mediated loss of MCL-1 expression and induction of BIM by the tumors. Moreover, xenograft studies indicate that cerdulatinib does not interfere with the anti-tumor activity of rituximab, suggesting that these two agents may combine well clinically to enhance anti-tumor activity. We report here updated results from a phase 2a dose expansion study in which cerdulatinib was evaluated as a single agent and initial results with cerdulatinib in combination with rituximab in r/r FL.

Methods: This is a phase 2a dose expansion study was carried out with cerdulatinib dosed 30 mg orally BID in patients with relapsed/refractory (r/r) B cell lymphoma. Dose reductions were permitted to a minimum of 15 mg BID. Responses of patients to the cerdulatinib treatment and cerdulatinib rituximab combination treatment were assessed by Lugano Classification criteria.

A total of 40 patients were enrolled in the single arm, cerdulatinib treatment cohort and 11 patients were enrolled in the cerdulatinib rituximab combination cohort. Median age was 64 (42-81) and median number of prior therapies was three (1-8). 50 (98%) patients had prior anti-CD20 therapy and 8 (16%) patients had prior PI3K or BTK inhibitors. The most common adverse effects (AEs) of any grade were diarrhea (47%), nausea (37%), lipase increase (29%) and amylase increase (22%). Grade 3+ AEs occurring in more than 5% patients are lipase increase (24%), diarrhea (12%), amylase increase (10%), nausea (8%), hypertension (8%), and neutropenia (6%). Grade 3+ infections occurred in 6 (12%) of patients. One patient had Grade 5 multi-organ failure potentially related to study drug. Amylase and lipase elevations generally were not associated with abdominal pain or pancreatitis. The safety profile in the combination cohort appeared to be similar to what is seen with single-agent cerdulatinib.

Responses observed for both cohorts included: an ORR of 46% (5 CRs and 13 PRs out of 40 patients) in the single arm cohort and an ORR of 67% (4 PRs out of 6 patients) in the combination cohort. Responses typically occurred after 2 cycles of treatment. Responses had been durable in the single arm cohort and 10 patients have been on drug for more than one year. All patients in the combination cohort remained on drug (up to 6 months).

In summary, data from the phase 2a does expansion study showed that the recommended cerdulatinib phase 2 dose of 30 mg BID had good tolerability and efficacy in heavily pre-treated r/r FL. The combination of cerdulatinib with rituximab was well tolerated and has led to tumor reductions in all patients evaluated, with both patients who achieved SD demonstrating more than 40% reduction in baseline target tumors at the first re-scan.

The disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed is:

1. A method of treating a T-cell lymphoma in a human patient in need thereof, comprising administering to the patient an effective amount of cerdulatinib or a pharmaceutically acceptable salt thereof.

2. The method of claim 1, wherein the T-cell lymphoma is relapsed or refractory T-cell lymphoma.

3. The method of claim 1, wherein the T-cell lymphoma has not been previously treated with an agent for treating T-cell lymphoma.

4. The method of claim 1, wherein the T-cell lymphoma is selected from peripheral T-cell lymphomas, angioimmunoblastic T-cell lymphoma, follicular T-cell lymphoma, anaplastic large cell lymphoma, enteropathy-associated T-cell lymphoma, adult T-cell leukemia/lymphoma, T-cell leukemia, nasal NK/T-cell lymphoma, hepatosplenic T-cell lymphoma, and cutaneous (skin) T-cell lymphoma.

5. The method of claim 1, wherein the T-cell lymphoma is relapsed or refractory peripheral T-cell lymphoma.

6. The method of claim 1, wherein the T-cell lymphoma is angioimmunoblastic lymphoma.

7. The method of claim 1, wherein the T-cell lymphoma is anaplastic large cell lymphoma.

8. The method of claim 1, wherein the T-cell lymphoma is hepatosplenic T-cell lymphoma.

9. The method of claim 1, wherein the T-cell lymphoma is enteropathy-associated T-cell lymphoma.

10. The method of claim 1, wherein the T-cell lymphoma is cutaneous T-cell lymphoma.

11. The method of claim 10, wherein the cutaneous T-cell lymphoma is mycosis fungoides or Sézary syndrome.

12. The method of claim 1, further comprising administering to the patient an effective amount of rituximab.

13. The method of claim 1, wherein the effective amount of cerdulatinib is from about 10 mg to about 45 mg daily.

14. The method of claim 1, wherein the effective amount of cerdulatinib is from about 15 mg to about 30 mg twice daily.

15. The method claim 1, wherein the effective amount of cerdulatinib is about 15 mg, 20 mg, 25 mg, or 30 mg twice daily.

* * * * *